United States Patent
Hesse

Patent Number: 4,772,433
Date of Patent: Sep. 20, 1988

[54] VITAMIN D ANALOGUES

[75] Inventor: Robert Hesse, Cambridge, Mass.

[73] Assignee: Research Institute for Medicine and Chemistry Inc., Cambridge, Mass.

[21] Appl. No.: 827,553

[22] Filed: Feb. 10, 1986

Related U.S. Application Data

[63] Continuation of Ser. No. 650,891, Sep. 17, 1984, abandoned, which is a continuation of Ser. No. 568,891, Jan. 6, 1984, abandoned, which is a continuation of Ser. No. 438,603, Nov. 2, 1982, abandoned.

[30] Foreign Application Priority Data

Nov. 2, 1981 [GB] United Kingdom ............ 8133018
Nov. 2, 1981 [GB] United Kingdom ............ 8133019

[51] Int. Cl.$^4$ .............................................. C07J 9/00
[52] U.S. Cl. ................................................ 260/397.2
[58] Field of Search ..................................... 260/397.2

[56] References Cited

U.S. PATENT DOCUMENTS 3,741,996 6/1973 DeLuca et al. ................. 540/126 X

OTHER PUBLICATIONS

The Merck Index, 9th Ed., 1976, pp. 9677–9680.
J. Org. Chem. (1976), vol. 41, Article by Aberhart et al., pp. 2098–2101.
"Chemistry Letters" (1976), pp. 583–586, Article by Yamalda et al.

Primary Examiner—Leonard Schenkman
Attorney, Agent, or Firm—Bacon & Thomas

[57] ABSTRACT

Compounds of the general formula

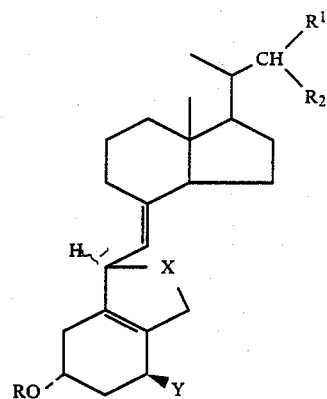

wherein R represents a hydrogen atom or a hydroxyl protecting group, Y represents a hydrogen atom or an optionally protected hydroxyl group, X represents the residue of a dienophile and either $R^1$ represents a halogen atom a hydrocarbylsulphonyloxy group or a group of the formula —Z—$R^3$ (in which Z represents —O—, —S—, —SO—, —$NR^4$— or —$CR^4R^5$— and $R^3$, $R^4$ and $R^5$, which may be the same or different, each represent a hydrogen atom or a straight or branched aliphatic group having 1-12 carbon atoms and which may optionally carry one or more substituents) and $R^2$ represents a hydrogen atom or $R^1$ and $R^2$ together represent an oxo group or an optionally substituted alkylidene group, except that $R^1$ and $R^2$ together with the group —CH(CH$_3$)CH— to which they are attached do not represent a group having the branched 17β-hydrocarbyl side chain skeleton of vitamin $D_2$ or vitamin $D_3$ or use in the preparation of novel vitamin D analogues.

5 Claims, 1 Drawing Sheet

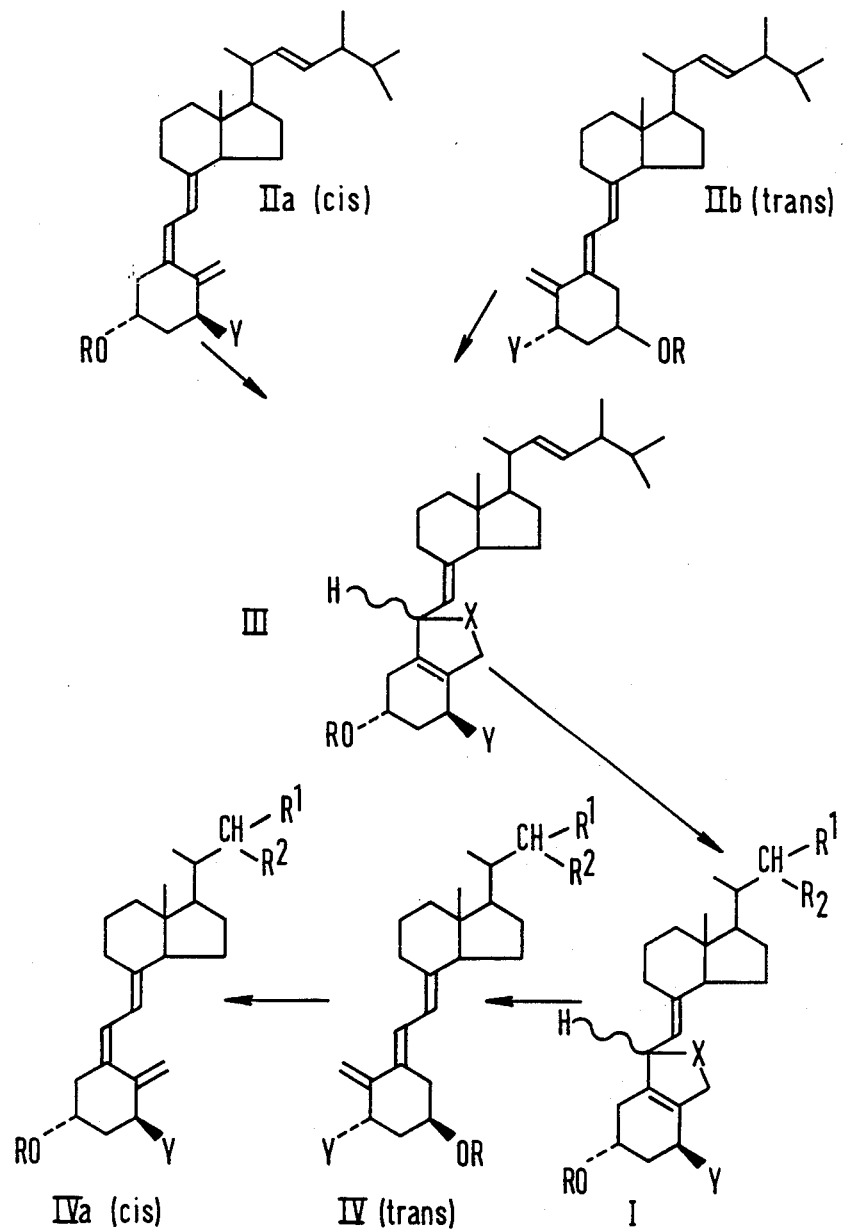

VITAMIN D ANALOGUES

This application is a comtinuation of U.S. patent application Ser. No. 650,891 filed Sept. 17, 1984, now abandoned, which is a continuation of U.S. patent application Ser. No. 568,891 filed Jan. 6, 1984, now abandoned, which is a continuation of U.S. patent application Ser. No. 438,603 filed Nov. 2, 1982, now abandoned.

This invention relates to novel intermediates in the production of vitamin D analogues and a method for their production.

In the past modified vitamin D derivatives have been prepared through modification of sterol precursors which are then converted into vitamin D derivatives through a standard series of steps, normally preliminary conversion of $\Delta^{5,7}$ dienes followed by irradiation of the dienes to give D vitamins. These procedures have serious flaws. First, all of the available methods for the synthesis of $\Delta^{5,7}$ dienes tend to give mixtures of products or require a number of steps and proceed in relatively low yield. The second difficulty is that the only known transformation of the 5,7 dienes into the vitamins involves irradiation followed by thermal equilibration. Iradiation intrinsically gives rise to a mixture of byproducts. This limits the yield of the desired vitamin and furthermore complicates its recovery in pure form.

Previous attempts to modify the 17-side chain of vitamin D compounds have been unsuccessful due to instability problems. We have now found that vitamin $D_2$ and related compounds can be converted to a protected form capable of withstanding the reaction conditions necessary for oxidative cleavage of the 22,23-double bond to form a 22-aldehyde which can then be converted to other derivatives as described hereinafter. In particular, we have found that vitamin $D_2$ compounds in either the cis or trans configuration can be stablised by formation of a Diels Alder dienophile adduct which can subsequently be reconverted to the trans form of the vitamin after the side-chain modification. The trans vitamin analogues can then be efficiently converted into the active cis form by known reactions.

According to one feature of the present invention we provide compounds of the general formula I,

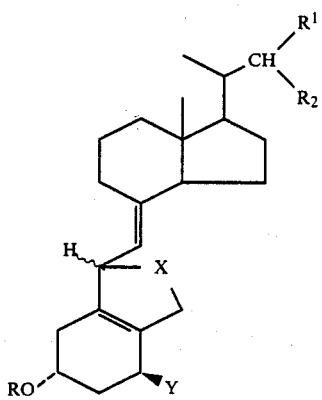

I wherein R represents a hydrogen atom or a hydroxyl protecting group, Y represents a hydrogen atom or an optionally protected hydroxyl group, X represents the residue of a dienophile and either $R^1$ represents a halogen atom a hydrocarbylsulphonyloxy group or a group of the formula $-Z-R^3$ (in which Z represents $-O-$, $-S-$, $-SO-$, $-NR^4-$ or $-CR^4R^5-$ and $R^3$, $R^4$ and $R^5$, which may be the same or different, each represents a hydrogen atom or a straight or branched aliphatic group having 1–12 carbon atoms and which may optionally carry one or more substituents) and $R^2$ represents a hydrogen atom or $R^1$ and $R^2$ together represent an oxo group or an optionally substituted alkylidene group, except that $R^1$ and $R^2$ together with the group $-CH(CH_3)CH-$ to which they are attached do not represent a group having the branched 17$\beta$-hydrocarbyl side chain skeleton of vitamin $D_2$ or vitamin $D_3$.

The above compounds are useful intermediates in the preparation of vitamin D analogues i.e. compounds of general formulae IV and IVa

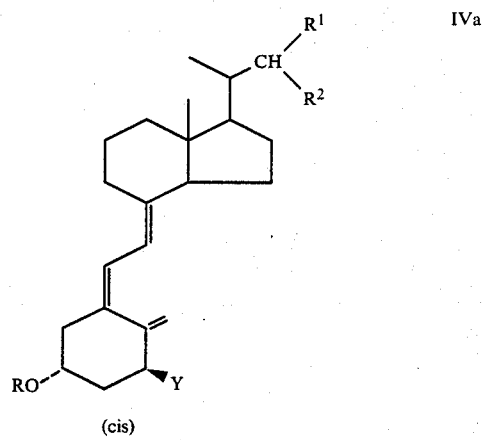

IVa (cis)

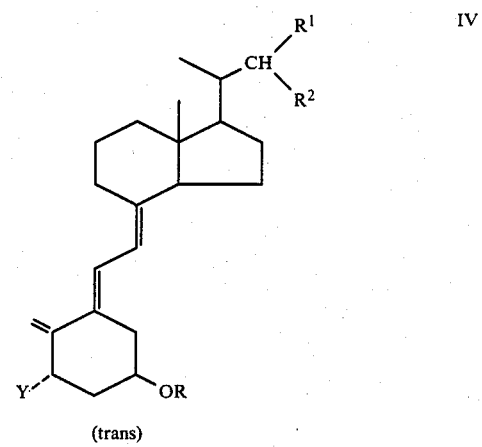

IV (trans)

wherein R, Y, $R^1$ and $R^2$ are as hereinbefore defined. The above compounds of general formulae IV and IVa are also novel and constitute a still further feature of this invention.

BRIEF DESCRIPTION OF THE DRAWING

The use of the compounds of general formula I in the preparation of the novel compounds of formulae IV and IVa is illustrated in the reaction scheme of the accompanying drawings, R, Y, X, $R^1$ and $R^2$ being as defined above. The compounds of formula I–IV may also carry further groupings.

It should be noted that the Diels Alder adduct formed from either the 5,6-cis- or the 5,6-transvitamin starting material exists as a mixture of two possible isomers at the 6-position. However, since the eventual removal of the Diels Alder residue always generates a compound of the 5,6- trans configuration, there is no need to distinguish between such 6-isomers or to effect their separation.

We have found that using the above procedure a wide range of groups $R^1$ may be introduced into the vitamin D structure. Thus, as indicated above $R^1$ may be a group of the formula $Z-R^3$, where Z is $-O-$, $-S-$, $-SO-$, $-NR^4$ or $-CR^4R^5-$ and $R^3$, $R^4$ and $R^5$, which may be the same or different, are each a hydrogen atom or a straight or branched aliphatic group having 1-12 carbon atoms which may carry one or more substituents such as, for example halogen atoms (e.g. fluorine), or optionally protected hydroxyl groups.

In general it is preferred that the group $R^3$ in the final products should be of the formula

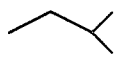

(in order to provide a 17β- side chain of approximately the shape present in natural vitamin D compounds) with the possibility of substitution as described above. The heteroatoms Z, where present, do not greatly change the overall shape of the side chain.

In particular, the invention enables compounds of formula IV and IVa to be prepared in which $R^1$ is of formula

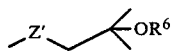

wherein Z' represents $-O-$, $-S-$, $-NH-$ or $-SO-$ and $R^6$ represents a hydrogen atom or a hydroxyl protecting group, the 1α-position optionally carrying a hydroxyl or protected hydroxyl group, these being analogues of the active metabolite 25-hydroxy vitamin $D_3$.

Protected hydroxyl groups may, for example, be acyl groups e.g. alkanoyl groups (preferably having 1-6 carbon atoms), aralkanoyl groups (preferably having 7-15 carbon atoms), aroyl groups (preferably having 6-12 carbon atoms), cyclic ether groups or trihydrocarbylsilyl groups. Examples of such groups include acetyl, propionyl, benzoyl and tetrahydropyranyl groups and trihydrocarbylsilyl groups having up to three $C_{1-6}$ alkyl, $C_{6-12}$ aryl and/or $C_{7-15}$ aralkyl groups.

The new synthetic analogues of the invention have modified vitamin D properties of interest in medicine.

The compounds of formulae IV and IVa in which $R^1$ has the above meanings may be prepared, inter alia, by nucleophilic substitution reactions on compounds of formula IV and IVa in which $R^1$ represents a halogen atom, such as a chlorine, bromine or iodine atom, or a leaving group, for example a hydrocarbylsulphonyloxy group $O-SO_2R^7$ in which $R^7$ represents, for example, an alkyl group (preferably having 1-6 carbon atoms), an aryl group (preferably having 6-12 carbon atoms) or an aralkyl group (preferably having 7-15 carbon atoms). The tosyloxy group is preferred. Alternatively, the above compounds may be prepared from corresponding compounds of formula I and the dienophile group X removed subsequently. Since, however, the nucelophilic substition reactions are mostly carried out in the presence of a base and since the protected compounds of formula I are less stable to base than the parent trienes of formula IV and IVa, the latter are commonly preferred substrates.

In the formation of 22-thia compounds (in which Z is $-S-$), the nucleophilic reagent is conveniently the thiol of formula $R^3XH$ reacted in an inert solvent such as tetrahydrofuran in the presence of a nonnucleophilic base, for example an inorganic base such as sodium hydride or an organic base such as pyridine.

The corresponding sulphoxides ($Z=-SO-$) may be prepared by oxidation of the thia-compound ($Z=-S-$), for example using a peracid or salt as oxidising agent, e.g. a periodate. Mixtures of the (R) and (S) sulphoxides are normally formed and the invention extends to these separately and in admixture.

The 22-oxa compounds of formula IV or IVa may be prepared by reaction of an alchol of formula I, IV or IVa in which $R^1$ is OH, with an alkylating agent or alternatively by reaction of a reactive derivative thereof, with an alcoholate; these reactions are followed by deprotection when a compound of formula I is used. The reactive derivative may, for example, be a halide such as an iodide, or a hydrocarbylsulphonyloxy derivative, such as a tosyloxy derivative, the alcoholate being, for example, an alkali metal or thallium alcoholate of the alcohol $R^3OH$. It is preferred, however, to react the compound of formula I, IV or Va in which $R^1$ is OH with an epoxide. This generates a side chain carrying a hydroxyl group derived from the epoxide oxygen. Where it is desired to make 25-hydroxy-22-oxa vitamin $D_3$ derivatives, a suitable reagent is isobutylene epoxide. The reaction is advantageously effected in an inert solvent, e.g. a hydrocarbon solvent such as benzene, in the presence of a non-nucleophilic base, conveniently an alkali metal t-alkoxide in the presence of a phase transfer agent such as a crown ether. Under such basic conditions, we have found it especially preferred to effect the reaction on a starting compound of formula IV or IVa, since the trienes are, as indicated above, more stable to these conditions than the dienophileprotected compounds of formula I.

The 22-aza compounds of formula I, IV or IVa may be prepared by reaction of a reactive derivative of an alcohol of formula I, IV or IVa in which $R^1$ is OH, for example a halide such as an iodide, or a hydrocarbylsulphonyloxy derivative such as a tosyloxy derivative, with an amine of formula $R^3R^4NH$. Due to the basicity of the reagent, a substrate of formula IV or IVa is preferred. Where the amine is liquid it is preferably reacted without added solvent.

The 22-aza derivatives may often conveniently be isolated as N-acylates, such as N-acetates, which may be formed by reaction with an appropriate acid anhydride.

The 22-hydrocarbylsulphonyloxy derivatives of formulae I, IV and IVa used in the above reactions may be prepared by reacting the corresponding alcohol with the appropriate hydrocarbylsulphonyl halide, e.g. tosyl chloride in the presence of a base such as pyridine. Best results have been obtained by effecting this reaction on a compound of formula I in which X is $SO_2$, and removing the $SO_2$ residue by thermolysis, as described hereinafter.

The compounds of formula I, IV or IVa in which Z in $R^1$ is $CR^4R^5$ may be prepared by reacting compounds of formula I, IV or IVa carrying a hydrocarbylsulphonyloxy group $R^1$, e.g. a tosyl group, with carbon nucleophiles. Suitable carbon nucleophiles are Grignard reagents reacted in the presence of a copper catalyst, e.g. a cuprous salt. Thus, for example, 25-hydroxy vitamin D₃ and the 1α-hydroxy derivative thereof may be prepared by reacting an appropriate hydrocarbylsulphonyloxy derivative of formula I, IV or IVa with a Grignard reagent of the formula

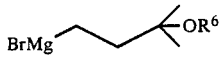

(where R⁶ has the above meaning) in tetrahydrofuran in the presence of cuprous iodide.

For the production of an alcohol of formula I in which R¹ is OH, for use in the preparation of the above novel vitamin D derivatives, the formyl group in the corresponding aldehyde of formula I (wherein R¹ and R² together represent oxo) must be reduced.

We have found that this can be effected readily, often in essentially quantitative yield, by reaction with a metal hydride reducing agent such as an alkali metal borohydride, e.g. sodium borohydride. It is noteworthy that this reduction retains the original configuration at the 20-carbon atom. Such alcohols are also new compounds.

Compounds of formula I, IV or IVa may also be prepared in which R¹ is a divalent alkylidene group, which may carry substituents as described above for R³. Thus, for example, the aldehyde of formula I (wherein R¹ and R² together represent oxo) may be reacted with an ylide, for example a Wittig reagent which may be represented by the general formula

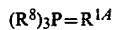

wherein the groups R⁸, which may be the same or different, are alkyl (preferably $C_{1-6}$), aralkyl (preferably $C_{7-15}$) or aryl (preferably $C_{6-12}$) groups and $R^{14}$ is an alkylidene group (preferably having 1 to 8 carbon atoms) and may carry substituents as described for R³ above.

The Wittig reagent will normally be formed in situ by reaction of a quaternary salt thereof with a strong base in an inert solvent. Suitable bases include hydrocarbyl lithium compounds such as phenyl lithium and n-butyl lithium. Suitable solvents include ether solvents such as tetrahydropyran and diethyl ether. The aldehyde of formula I is preferably added immediately after the Wittig reagent has been formed.

The phosphonium salt precursor of the appropriate Wittig reagent for formation of the correct 17β-side chain of 25-hydroxy vitamin D₃ may, for example be prepared by reaction of isobutylene epoxide with methylenetriphenylphosphorane; the initially formed product in which R⁵ is H may if desired be protected, for example by formation of a tetrahydropyranyl or trihydrocarbylsilyl derivative. The phosphorane is preferably prepared by reaction of methyltriphenylphosphonium bromide in a cyclic ether solvent such as tetrahydrofuran in the presence of a strong base such as phenyl or n-butyl lithium, the isobutylene epoxide then being reacted in situ with a second equivalent of base. We have found the phosphonium bromide initially produced to be difficult to isolate and purify but that conversion to a tetraphenylborate salt enabled a relatively pure product to be obtained.

If it is desired to form a saturated side-chain, selective reduction of the newly formed 22,23-double bond is required. This was unexpectly found to be possible using hydrogenation over 5% palladium on charcoal. It is noteworthy that this reduction restores the desired, "natural" configuration at the 22- and 23- carbon atoms. This route thus provides a further method of preparing compounds of formula I, IV or IVa in which R¹ is -CR³R⁴R⁵, as defined above.

It will be seen that the compounds of formula I in the above reaction scheme are key intermediates in the production of the new vitamin D analogues according to the invention. By way of illustration their preparation is now described in detail starting from vitamin D₂ or its 5,6-trans isomer.

The compound of formula III may be prepared by reaction of a vitamin D₂ compound of formula IIa or IIb with a dienophile whereby the desired divalent grouping X is introduced.

The dienophile may, for example, be SO₂ or a diacylazo compound. Preferred azo dienophiles are cyclic azo compounds such as phthazine diones or triazoline diones; in general these may be represented by the formula V,

where W is a divalent aromatic carbocyclic group such as a 1,2-phenylene group or a group >N-R⁹ where R⁹ is an aryl group such as a phenyl group. The divalent aromatic group or the aryl group R⁹ may carry substituents, for example $C_{1-6}$ alkyl or alkoxy groups, halogen atoms or nitro groups. Derivatives of formula III in which X is of formula V are also new compounds.

Where the dienophile is SO₂, this may simply be reacted with the vitamin D₂ compound in a suitable solvent, for example aqueous media capable of dissolving the vitamin. A well stirred mixture of water and a hydrocarbon solvent such as benzene is particularly useful. Basic conditions are preferably used, e.g. using an inorganic base such as an alkali metal bicarbonate. Where the dienophile is a cyclic azo compound of formula V in which W is a group >N-R⁹, this may be added to the starting vitamin D₂ compound in solution in a suitable solvent such as ethyl acetate. Where W is a divalent-1,2-arylene grouping as in phthalazine 1,2-dione, however, this is preferably formed in situ by oxidation of the corresponding cyclic hydrazide, e.g. phthalhydrazide. Thus the vitamin D₂ compound may be reacted in solution in an inert solvent such as a halogenated hydrocarbon with the cyclic hydrazide in the presence of an oxidising agent such as lead tetraacetate/acetic acid.

After formation of the adduct of formula III, the 22,23-double bond may be cleaved to form the 22-formyl derivative of formula I by known oxidative techniques such as permanganate/periodate, osmate/periodate or, most preferably ozonolysis. We have found that this reaction proceeds selectively in high yield with little cleavage of the 7,8-double bond and, in particular, with no disturbance of the stereochemistry at the 20-position.

Ozonolysis may be effected by passing ozone, preferably diluted with a further gas such as oxygen, through a solution of the compound of formula III in a solvent therefor to form an ozonide which is then reductively cleaved by a suitable reducing agent. A suitable solvent is, for example, a halogenated hydrocarbon such as dichloromethane, a ketone, e.g. methyl ethyl ketone or acetone or an alcohol such as methanol or ethanol. A mixture of dichloromethane and methanol gave especially good yields. The reducing agent may be present during the reaction or added after ozonide formation is completed. Thus, for example tetracyanoethylene may be present in solution in acetone during ozonolysis. While reducing agents such as dimethyl sulphide may be used to reduce the ozonide after its formation, preferred reagents are trivalent phosphorus compounds such as triphenylphosphine.

Where an alcohol solvent is used, the aldehyde product of formula I may form an acetal derivative with the alcohol. This may, however, readily be cleaved hydrolytically, for example using an aqueous base e.g. sodium bicarbonate. The reaction is preferably carried out at low temperatures, for example −78° C.

After modification of the 17-side chain, the dienophile residue X may be removed to yield, as indicated above, a 5,6-trans vitamin of general formula IV. The removal of the residue X will be effected in different ways, depending on its nature.

Where X is $SO_2$, it is conveniently removed by thermolysis under basic conditions, e.g. in the presence of a hydroxylic solvent such as an alcohol, e.g. ethanol, containing a base such as an alkali metal carbonate, e.g. sodium carbonate.

Where X is a group of formula V, removal can readily be effected by removal of the —CO—W—CO— moiety, for example by basic hydrolysis or treatment with hydrazine, followed by mild oxidation of the unsubstituted vitamin hydrazide so formed to the corresponding azo-compound which spontaneously decomposes to yield the required 5,6,-trans vitamin. Basic hydrolysis can be effected using strong alkali such as sodium or potassium hydroxide, for example in solution in an alcohol such as methanol, or by treatment with an amine such as triethylamine. The preferred method, however, is treatment with hydrazine which produces the desired hydrazide in high yield; this reaction has not previously been described for decomposition of such Diels-Alder adducts. Oxidation may be effected using reagents capable of oxidising hydrazo compounds to azo compounds, for example ceric, cupric, ferric, ferricyanic or periodate salts or air. A preferred mild reagent, however, is a diaryl telluroxide such as dianisyl telluroxide, preferably used with a reoxidant such as 1,2-dibromotetrachloroethane and a base such as $K_2CO_3$ as described in our British Patent Specification No. 2058758A.

Where a 1α-hydroxy vitamin D compound is required, the modified 5,6-trans-vitamin compound of formula IV, which carries the desired 17-side chain, optionally protected, may be subjected to 1α-hydroxylation, using the procedure of our South African patent No. 79/5958. Thus, the 5,6-trans vitamin compound may be reacted with a selenite ester, preferably formed in situ by reaction of selenium dioxide and an alcohol such as methanol. The quantity of selenium compound may be reduced if a re-oxidant is employed, for example a periodate salt or N-methyl morpholine 1-oxide.

Alternatively, a reactive derivative of a 22hydroxy derivative of formula I or IV above may be 1α-hydroxylated by the above procedure and the desired side-chain built up subsequently.

The 5,6-trans vitamin D compound of formula IV, after modifications such as those described above, may readily be isomerised in high yield to a required active cis-vitamin compound by known techniques, for example by irradiation in the presence of iodine or diphenyl selenide or, preferably, a triplet photosensitizer having a triplet energy of the order of 45± 5 Kcal per mole, such as anthracene, acridine or phenazine. To avoid isomerisation to undesired tachysterol derivatives, acid conditions should be avoided and the photoisomerisation is preferably effected in the presence of a base such as triethylamine.

Where protected hyroxyl groups are present in the vitamin product, these may be removed by conventional methods. In general, the vitamin structure is somewhat sensitive to acids, but is resistant to basic conditions and the latter are advantageously used. Acyloxy groups can thus be removed using alkali metal hydroxide in an alcohol solvent such as methanol. Silyl groups may be removed by treatment with quaternary ammonium fluorides such as tetra-n-butylammonium fluoride. Since most of the reactions decribed above can be applied to compounds having unprotected hydroxyl groups, protecting groups may be removed, if desired, at various stages. Although the vitamins are resistant to bases (and sensitive to acids), the dienophile adducts tend to be sensitive to bases and relatively resistant to acids. Consequently, acid contitions may be used to deprotect hydroxyl groups at stages where the dienophile residue X is present.

In general, most of the stages described above proceed in excellent yield. When conditions are optimised, yields of the order of 80% or more at each stage have been achieved. This renders the overall yield of modified vitamin, starting from vitamin $D_2$, markedly better than those achieved using many previously suggested routes.

The following Examples are given by way of illustration only:

Microanalyses and mass spectra were obtained by the staff at the Institut de Chemie des Substances Naturelles du CNRS, Gif-sur-Yvette, France. Melting points were determined using either a Kofler block, Mel-Temp or Fisher-Johns apparatus and are uncorrected. Optical rotations were measured at room temperature using a Rudolph Photoelectric Polarimeter, Model 70, and are reported for chloroform solutions unless otherwise stated. UV spectra were recorded using a Carey 11 spectrophotometer and are reported for ethanol solutions. The molar extinction coefficient ($\epsilon$) for these absorbances are given in parenthesis. IR spectra were recorded using a Perkin-Elmer 137 "Infracord" spectrophotometer and are reported for KBr discs unless otherwise stated. Absorbance characteristics are denoted by s=strong, m=medium, w=weak, sh=shoulder, br=broad. $^1$Hnmr spectra were determined at 60 MHz on a Varian T-60 spectrometer. NMR characteristics are denoted as s=singlet, d=doublet, tr=triplet, q=quartet, m=multiplet, W=peak width at half height and are reported for $CDCl_3$ solutions, unless otherwise indicated, with tetramethylsilane as internal standard, as values of δ (ppm downfield of TMS).

Thin layer chromatography (tlc) was carried out on 250μ silica gel GHLF "Uniplates" (Analtech, USA); and preparative layer chromatography (plc) on 1 mm silica gel GF-254 "Uniplates" (Analtech, USA). "Chromatography" refers to medium pressure liquid chromatography carried out using E. Merck silica gel 60H.

High performance liquid chromatography (HPLC) was carried out using Waters Associates silica gel "Porasil A" packed in two 2 ft×⅜ inch stainless steel columns, and a Waters Associates chromatograph, equipped with a 6000 psi pump and a differential refractometer detector. Ozone was generated from a Towers Ozone Apparatus GE-150. Selective ozonolysis requires vigorous mixing of the dissolved substrate and the oxygen-ozone gaseous mixture. A "Vibromixer" (Chemapag, Switzerland) equipped with a stainless steel gas inlet/stirrer was particularly useful for this purpose. This equipment was also used for the formation of the phthalazine-1,4-dione Diels-Alder adducts of vitamin D.

A 200 W Hanovia medium pressure mercury vapor lamp (654A36) was used as irradiation source for 5,6-double bond photoisomerisation reactions.

Reactions on calciferol substrates were routinely performed under an inert, argon atmosphere. Calciferols were stored at −20° C., under argon, in the dark, as either crystalline solids or (where possible) ether solutions. Solvents used were reagent grade unless otherwise stated.

Aqueous work-up refers to partition between an organic solvent and water, followed by sequential washing with a 5% aqueous sodium bicarbonate solution and a saturated aqueous sodium chloride solution. The organic solution was dried using either anhydrous MgSO$_4$ or anhydrous Na$_2$SO$_4$, and the solvent removed on a rotary evaporator. Acid work-up refers to partition between an organic solvent and water, followed by sequential washing with a 4% aqueous HCl solution; 5% aqueous sodium bicarbonate solution, etc. as for aqueous work-up.

EXAMPLE 1

(a)

6(R),19-[4'-phenyl-1',2',4'-triazolidine-3',5'-dione-1',2'-yl]-9,10-seco-3β-hydroxy-ergosta-5(10), 7(E), 22(E)-triene To ergocalciferol (5 g) in ethylacetate (150 ml) at 0° C. under an argon atmosphere, 4-phenyl-1,2,4-triazoline-3,5-dione (2.4 g, 1.1 eq) in ethyl acetate (150 ml) was added over 45 min. After a further 1 hr, some of the title adduct had precipitated. The mixture was filtered and the filtrate passed down a neutral alumina column. Elution with hexane/ethylacetate gave the remainder of the product. Crystallisation from alcohol gave 6.2 g (86%). mp 99° C.; [α]$_D$ = +208° (c=0.76); $^1$Hnmr δ 7.48 (s, 5H, aryl), 5.22 (m, W=10 Hz, C-22H, 23H), 4.98 and 4.73 (an AB system, J=10 Hz, C-6H, 7H), 4.2 and 3.85 (an AB system, J=15 Hz, C-19H$_2$), 4.1 (m, C-3H), 0.53 (s, C-18H$_3$). IR νmax (CHCl$_3$) 3700 (br), 2950 (s), 1775 (m), 1710 (s), 1425 (s)cm$^{-1}$; mass spec. molecular ion, m/e=571; (analysis found: % C, 75.63; H, 8.62; N, 7.36; C$_{36}$H$_{49}$O$_3$N$_2$; requires: % C, 75.62.; H, 8.64; N, 7.35).

Similarly prepared from ergocalciferol acetate in 85% yield was the corresponding acetate 6(R),19-[4'-phenyl-1',2',4'-triazolidine-3',5'-dione-1',2'-yl]-9,10-seco-3β-acetoxy-ergosta-5(10), 7(E), 22(E)-triene.

Crystallised from ethanol. m.p.85° C.; [α]$_D$ = +183° (c=0.82); $^1$Hnmr δ 7.48 (s, 5H, aryl), 5.22 (m, W=12 Hz, C-3H, 22H, 23H), 4.98 and 4.73 (an AB system, J=10 Hz, C-6H, 7H), 4.2 and 3.85 (an AB system J=16 Hz, C-19H$_2$), 2.0 (s, OAc), 0.53 (s, C-18H$_3$); IR νmax (CHCl$_3$) 2950 (s), 2900 (sh), 1725 (s), 1420 (m)cm$^{-1}$; mass spec. molecular ion m/e=613; (analysis found: % C, 74.18; H, 8.11; N, 6.65; C$_{38}$H$_{51}$O$_4$N$_3$; requires: % C, 74.35; H, 8.38, N, 6.85).

(b) Ozonolysis

The adduct from (a) above (250 mg) in acetone (10 ml) containing tetracyanoethylene (55 mg, 1 eq) at −78° C. was treated with ozone for 3 min (approx. 1.5 eq). The system was purged with argon whilst warming to room temperature. The product mixture was separated by plc to give 130 mg of starting material (nmr) and the corresponding 20(S)-formyl derivative (90 mg, 84%) as a white foam. $^1$Hnmr δ 9.55 (d, J=3.75 Hz, C-22H), 7.45 (s, 5H, aryl), 5.15 (m, W=12 Hz, C-3H), 4.92 and 4.82 (an AB system, J=10 Hz, C-6H, 7H), 4.18 and 4.70 (an AB system J=16 Hz, C-19H$_2$), 2.0 (s, OAc), 1.12 (d, J=7H) C-21H$_3$), 0.57 (s, C-18H$_3$).

EXAMPLE 2

(a) Reaction of erocalciferol acetate with phthalazine-1,4-dione

Phthalhydrazide (10 g, 2.5.eq) was suspended in a solution of ergocalciferolacetate (10 g) in dry CH$_2$Cl$_2$ (200 ml). The efficiently mixed mixture was cooled to 0° C., and a solution of lead tetra-acetate (20 g) in dry CH$_2$Cl$_2$ (100 ml) and acetic acid (1 ml) was added dropwise. The reaction was monitored by tlc. Upon completion, the residual phthalhydrazide was filtered off. Aqueous work-up followed by careful crystallisation from ethylacetate gave 7.4 g (54%) of 6(R),19-[N,N'-phthalhydrazido]-9,10-seco-3β-acetoxy-ergosta-5(10), 7(E), 22(E)triene. m.p. 202°-203° C.; [α]$_D$ = +343° (c=1.02): UV λmax 238 nm (38,250) and 312 nm (11,300); $^1$Hnmr δ 8.3 (m, W=12 Hz, 2H, aryl), 7.8 (m, W=10 Hz, 2H, aryl), 5.9 (d, J=10 Hz, C-7H), 5.08.(m, W=10 Hz, C-3H 22H, 23H), 4.78 and 4.22 (an AB system, J=18 Hz, C-19H$_2$), 4.75 (d, J=10 Hz, C-6H), 2.0 (s, OAc), 0.13 (s, C-18H$_3$); IR νmax 2950 (s), 2900 (sh), 1750 (s), 1660 (s), 1610 (m), 1380 (m), 1355 (m), 1250 (s)cm$^{-1}$; mass spec. molecular ion m/e=598: (analysis found: % C, 75.92; H, 8.30; N, 4.61; C$_{38}$H$_{50}$O$_4$N$_2$ requires: % C, 76.22, H, 8.42; N, 4.68). The mother liquors were chromatographed on silica gel to give 3.6 g (26%) of essentially pure 6(S),19-[N,N'-phthalhydrazido]-9,10-seco-3β-acetoxy-ergosta5(10), 7(E), 22(E)-triene. Solid from CH$_2$Cl$_2$/hexane. m.p. 114°-116° C.; [α]$_D$ = −306° (c=0.64); $^1$Hnmr δ 8.3 (m, W=12 Hz, 2H, aryl), 7.8 (m, W=10 Hz, 2H, aryl), 6.0 (d, J=10 Hz, C-7H), 5.2 (m, W=10 Hz, C-3H, 22H, 23H), 4.83 (d, J=10 Hz, C-6H), 4.78 and 4.23 (an AB system, J=18 Hz, C-19H$_2$), 2.17 (s, OAc), 0.65 (s, C-18H$_3$); IR νmax 2950 (s), 900 (sh), 1660 (s), 1610 (m), 1380 (m), 1355 (m,), 1250 (s)cm$^{-1}$; mass spec. molecular ion m/e=598.

(b)

6(R),19-[N,N'-phthalhydrazido]-9,10-seco-3β-hydroxy-ergosta-5(10), 7(E), 22(E)-triene To the acetate from (a) above (5 g) in benzene (100 ml) were added NaOH/CH$_3$OH (1.25 M solution, 12 ml). After 20 min, the mixture was diluted with water and CH$_2$Cl$_2$. Acid work-up gave an essentially quantitative yield (4.5 g) of the title 3β-hydroxy compound, crystalline from CH$_2$Cl$_2$/ether. m.p. 169°-171° C.; [α]$_D$ = +392° (c=0.773); $^1$Hnmr δ 8.3 (m, W=12 Hz, 2H, aryl), 7.8 (m, W=10 Hz, 2H, aryl), 5.9 (d, J=10 Hz, C-7H), 5.12 (m, W=9 Hz, C-22H, 23H), 4.78 and 4.22 (an AB system, J=18 Hz, C-19H$_2$), 4.75 (d, J=10 Hz, C-6H), 4.1 (m, C-3H), 0.18 (s, C-18H$_3$). IR $\nu$max 3550 (br), 2950 (s), 2900 (sh), 1650 (s), 1610 (m), 1375 (m), 1350 (m)cm$^{-1}$; mass spec molecular ion m/e=556; (analysis found: % C, 77.76; H, 8.78, N, 5.17 C$_{36}$H$_{48}$O$_3$N$_2$ requires: % C: 77.66; H, 8.69; N, 5.03.

(c)
6(R):19-[N,N'-phthalhydrazido]-9,10-seco-3$\beta$-tetrahydropyranyloxyergosta-5(10), 7(E), 22(E)-triene The alcohol from (b) above (4.5 g) in benzene (100 ml) was stirred overnight with dihydropyran (10 ml) and p-toluene sulphonic acid (10 mg). Aqueous work-up gave the title THP ether (204c) (5 g, 96%). Crystalline from CH$_2$Cl$_2$/ether. m.p. 151°–154° C.; [$\alpha$]$_D$= +332° (c=1.25); $^1$Hnmr $\delta$ 8.3 (m, W=12 Hz, 2H, aryl), 7.8 (m, W=10 Hz, 2H, aryl), 5.9 (d, J=10 Hz, C-7H), 5.07 (m, W=9 Hz, C-22H, 23H), 4.78 and 4.22 (an AB system, J=18 Hz, C-19H$_2$), 4.75 (d, J=10 Hz, C-6H), 4.7 (m, THP, C-2'H), 4.02 (m, C-3H), 3.5 (m, W=20 Hz, THP, C-6'H$_2$). 0.17 (s, C-18H$_3$); IR $\nu$max 2950 (s), 2900 (sh), 1650 (s), 1610 (m), 1370 (s], 1350 (s), 1030 (s)cm$^{-1}$; mass spec. molecular ion m/e=640.

(d)
6(R),19-[N,N'-phthalhydrazido]-9,10-seco-3$\beta$-[t-butyldimethylsilyloxy]-ergosta-5(10), 7(E), 22(E)-triene The alcohol from (b) above (4.5 g) in CH$_2$Cl$_2$ (20ml) was treated with tbutyldixethylsilylchloride (1.9 g) and imidazole (2.7 g) at room temperature for 1.5hr. Addition of water followed by acid work-up and crystallisation from CH$_2$Cl$_2$/hexane gave 5.1 g (94%) of the silyl ether. m.p. 203°–205° C.; [$\alpha$]$_D$= +313° (c=1.5); $^1$Hnmr $\delta$ 8.3 (m, W=12 Hz, 2H, aryl), 7.8 (m, W=10 Hz, 2H, aryl), 5.9 (d, J=10 Hz, C-7H), 5.08 (m, W=9 Hz, C-22H, 23H), 4.78 and 4.22 (an AB system, J=18 Hz, C-19H$_2$), 4.75 (d, J=10 Hz, C-6H), 4.03 (m, C-3H), 0.88 (s, t-butyl), 0.17 (s, C-18H$_3$), 0.07 (s, Si-CH$_3$), 0.05 (s, Si-CH$_3$); IR $\nu$max 2950 (s), 2900 (sh), 1650 (s), 1610 (m), 1370 (s), 1350 (s), 1090 (s)cm$^{-1}$; mass spec. molecular ion m/e=670; (analysis found: % C, 74.98; H, 9.26; N, 4.13; C$_{42}$H$_{62}$O$_3$N$_2$Si requires: % C, 75.18; H, 9.31; N, 4.18.

(e)
6(R),19-[N,N'-phthalhydrazido]-9,10-seco-3$\beta$-methoxyethoxymethoxyergosta-5(10), 7(E), 22(E)-triene The alcohol from (b) above (4.5 g) in CH$_2$Cl$_2$ (100 ml) was stirred overnight at room temperature with methoxyethoxymethylchloride (8 ml) in the presence of diisopropylethylamine (20 ml). Acid work-up followed by chromatography and crystallisation from CH$_2$Cl$_2$/hexane gave 4.3 g (83%) of the MEM ether. m.p. 123°–125° C.; [$\alpha$]$_D$= +325° (c=1.295); $^1$Hnmr $\delta$ 8.3 (m, W=12 Hz, 2H, aryl), 7.8 (m, W=10 Hz, 2H, aryl), 5.9 (d, J=10 Hz, C-7H), 5.15 (m, W=9 Hz, C-22H, 23H), 4.82 (s, —OCH$_2$O—), 4.78 and 4.22 (an AB system, J=18 Hz, C-19H$_2$), 4.75 (d, J=10 Hz, C-6H), 4.0 (m, C-3H), 3.67 (m, W=6 Hz, —OCH$_2$CH$_2$O—), 3.43 (s, OCH$_3$), 0.18 (s, C-18H$_3$); IR $\nu$max 2950 (s), 2900 (sh), 1650 (s), 1610 (m), 1470 (m), 1450 (m), 1370 (s), 1340 (s), 1100 (s), cm$^{-1}$; mass spec. molecular ion m/e=644; (analysis found: % C, 74.72; H, 8.57; N, 4.13; C$_{40}$H$_{56}$O$_5$N$_2$ requires: % C, 74.50; H, 8.75; N, 4.34.

(f) General procedure for the ozonolysis of the ergostane side chain

The adduct (from (a), (c), (d) or (e) above (4–5 g) in CH$_2$Cl$_2$ (180 ml) and methanol (60 ml) was cooled to −78° C. The efficiently mixed solution was treated with an ozone-oxygen mixture (approx. 1 mmol O$_3$/min) for 8–12 min (tlc control) and then thoroughly purged with dry argon for approx. 5 min. Triphenyl phosphine (2.5–3 g) was added and the mixture, after approx. 30 min at −78° C. (tlc monitoring of the breakdown of the methoxyhy intermediates) was shaken with 5% aqueous NaHCO$_3$ (to prevemt dixethyl acetal formation) and allowed to warm to room temperature. The layers were separated and the organic solution dried. Chromatography through silica gel (40–50 g) gave the aldehyde (75–86%) free from any of the C-20(R) epimer (nmr). The following compounds were prepared in this manner.

(1)
6(R),19-[N,N'-phthalhydrazido]-9,10-seco-3$\beta$-acetoxy-20(S)-formylpregna-5(10), 7(E)-diene Crystalline from CH$_2$Cl$_2$/ether. m.p. 192°–193° C.; [$\alpha$]$_D$= +382° (c=1.235); $^1$Hnmr $\delta$ 9.55 (d, J=3 Hz, C-22H), 8.3 (m, W=12 Hz, 2H, aryl), 7.8 (m, W=10 Hz, 2H, aryl), 5.9 (d, J=10 Hz, C-7H), 5.17 (m, C-3H), 4.78 and 4.22 (an AB system, J=18 Hz, C-19H$_2$), 4.75 (d, J=10 Hz, C-6H), 2.07 (s, OAc), 1.07 (d, J=7 Hz, C-21H$_3$). 0.22 (s, C-18H$_3$); IR $\nu$max (CHCl$_3$) 2950 (m), 2900 (sh), 1740 (s), 1645 (s), 1610 (m), 1370 (m), 1350 (m), cm$^{-1}$; mass spec. molecular ion m/e=530: (analysis found: % C, 72.13; H, 7.12; N, 5.20; C$_{32}$H$_{38}$O$_5$N$_2$ requires % C, 72.43; H, 7.22; N, 5.28).

(21)
6(R),19-[N,N'-phthalhydrazido]-9,10-seco-3$\beta$-tetrahydropyranyloxy-20(S)-formyl-pregna-5(10), 7(E)-diene Crystalline from CH$_2$Cl$_2$/ether. m.p. 154°–156° C.; [$\alpha$]$_D$= +356° (c=0.84); $^1$Hnmr $\delta$ 9.42 (d, J=3 Hz, C-22H), 8.3 (m, W=12 Hz, 2H, aryl), 7.8 (m, W=10 Hz, 2H, aryl), 5.9 (d, J=10 Hz, C-7H), 4.78 and 4.22 (an AB system, J=18 Hz, C-19H$_2$). 4.75 (d, J=10 Hz, C-6H), 4.69 (m, THP, C-2'H), 4.0 (m, C-3H), 3.5 (m, W=18 Hz, THP, C-6'H$_2$), 0.95 (d, J=6 Hz, C-21H$_3$), 0.23 (s, C-8H$_3$). IR $\nu$max 2950 (s), 2900 (sh), 1725 (s), 1640 (s), 1610 (m), 1370 (m), 1350 (m), 1025 (s), cm$^{-1}$; mass spec. molecular ion m/e=572; (analysis found: % C, 72.89; H, 7.58; N, 4.78; C$_{35}$H$_{44}$O$_5$N$_2$ requires: % C, 73.40; H, 7.74; N, 4.89).

(3)
6(R),19-[N,N'-phthalhydrazido]-9,10-seco-3$\beta$-[t-butyldimethylsilyloxy]-20(S)-formyl-pregna-5(10), 7[E)-diene Crystalline from CH$_2$Cl$_2$/hexane. m.p. 195°–197° C.; [$\alpha$]$_D$= +335° (c=1.64); $^1$Hnmr $\delta$ 9.52 (d, J=3 Hz, C-22H), 8.3 (m, W=12 Hz, 2H, aryl), 7.8 (m, W=10 Hz, 2H, aryl), 5.9 (d, J=10 Hz, C-7H), 4.78 and 4.22 (an AB system, J=18 Hz, C-19H$_2$), 4.75 (d, J=10 Hz, C-6H), 4.07 (m, C-3H), 1.07 (d, J=7 Hz, C-21H$_3$), 0.88 (s, t-butyl), 0.22 (s, C-18H$_3$), 0.07 (s, Si-CH$_3$), 0.03 (s, Si-CH$_3$); IR $\nu$max 2950 (s), 2900 (sh), 1740 (s), 1650 (s), 1610 (s), 1350 (s), 1090 (s), cm$^{-1}$; mass spec. molecular ion m/e=602; (analysis found: % C, 71.57; H, 8.49; N, 4.51; C$_{36}$H$_{50}$O$_4$N$_2$Si requires: % C, 71.72: H, 8.36; N, 4.65).

(4)
6(R),19-N,N'-phthalhydrazido]-9,10-seco-20(S)-formyl-3$\beta$-methyoxyethoxymethoxy-pregna-5(10), 7(E)-diene Crystalline from CH$_2$Cl$_2$/hexane. m.p. 136°–137° C.: [$\alpha$]$_D$= +327° (c=0.62); $^1$Hnmr $\delta$ 9.49 (d, J=3 Hz, C-

22H), 8.3 (m, W=12 Hz, 2H, aryl), 7.8 (m, W=10 Hz, 2H, aryl), 5.9 (d, J=10 Hz, C-7H), 4.87 (s, —OCH$_2$O—), 4.78 and 4.22 (an AB system, J=18 Hz, C-19H$_2$). 4.75 (d, J=10 Hz, C-6H), 4.03 (m, C-3H), 3.7 (m, W=6 Hz, —OCH$_2$CH$_2$O—), 3.47 (s, OCH$_3$), 1.07 (d, J=Hz, C-21H$_3$), 0.22 (s, C-18H$_3$); IR $\nu$max 2950 (m), 2900 (sh), 1740 (m), 1650 (s), 1610 (m), 1370 (m), 1350 (m), 1030 (m).

EXAMPLE 3

General procedure for the reduction of the C-20(S)-formyl to the C-20(S)-(hydroxymethyl) derivative The aldehyde compound (2.5–3.5 g) in benzene (60–90 ml) was added dropwise over a 15–20 min period to NaBH$_4$ (0.8–1.0 g) in ethanol (20–30 ml). After the addition, the excess reducing agent was carefully quenched with dilute aqueous HCl. The mixture was diluted with CH$_2$Cl$_2$. Aqueous work-up gave the desired alcohol in essentially quantitative yield. The following compounds have been prepared in this manner.

(1)

6(R),19-[N,N'-phthalhydrazido]-9,10-seco-3$\beta$-acetoxy-20(S)-[hydroxymethyl]-pregna-5(10), 7(E)-diene Crstalline from CH$_2$Cl$_2$/ether. m.p. 238°–240° C.; [$\alpha$]$_D$= +363° (c=0.875); $^1$Hnmr $\delta$ 8.3 (m, W=12 Hz, 2H, aryl), 7.8 (m, W=10 Hz, 2H, aryl), 5.9 (d, J=10 Hz, C-7H), 5.07 (m, C-3H), 4.78 and 4.21 (an AB system, J=18 Hz, C-19H$_2$), 4.75 (d, J=10 Hz, C-6H), 3.47 (m, W=14 Hz, C-22H$_2$), 2.05 (s, OAc), 1.0 (broad singlet, C-21H$_3$), 0.17 (s, C-18H$_3$); IR $\nu$max (CHCl$_3$) 3200 (br), 2950 (m), 2900 (sh), 1750 (m), 1650 (s), 1610 (m), 1380 (m), 1350 (m), cm$^{-1}$; mass. spec. molecular ion m/e=532.

(2)

6(R),19-[N,N'-phthalhydrazido]-9,10-seco-20(S)-[hydroxymethyl]-3$\beta$-tetrahydropyranyloxy-pregna-5(10), 7(E)-diene Crystalline from CH$_2$Cl$_2$/ether. m p. 170°–173° C.; [$\alpha$]$_D$= +341° (c=0.58); $^1$Hnmr $\delta$ 8.3 (m, W=12 Hz, 2H, aryl), 7.8 (m, W=10 Hz, 2H, aryl), 5.9 (d, J=10 Hz, C-7H), 4.78 and 4.22 (an AB system, J=18 Hz, C-19H$_2$), 4.75 (d, J=10 Hz, C-6H), 4.67 (m, THP, C-2'H), 4.0 (m, C-3H), 3.5 (m, W=18 Hz, C-22H$_2$, THP, C-6'H$_2$), 1.0 (broad singlet, C-21H$_3$), 0.19 (s, C-18H$_3$); IR $\nu$max 3600 (br), 2950 (s), 2900 (sh), 1650 (s), 1610 (m), 370 (m), 1350 (m), 1025 (m), cm$^{-1}$; mass spec. molecular ion m/e=74; (analysis found : % C 72.96; H, 7.96; N, 4.73; C$_{35}$H$_{46}$O$_5$N$_2$ requires: C, 73.14; H, 8.07; N, 4.87).

(3)

6(R),19-[N,N'-phthalhydrazido]-9,10-seco-3$\beta$-[t-butyldimethylsilyloxy]-20(S)-[hydroxymethyl]-pregna-5(10), 7(E)-diene Crystalline from CH$_2$Cl$_2$/hexane. m.p. 145°–148° C., [$\alpha$]$_D$= +312° (c=1.22); $^1$Hnmr $\delta$ 8.3 (m, W=12 Hz, 2H, aryl), 7.8 (m, W=10 Hz, 2H, aryl), 5.9 (d, J=10 Hz, C-7H), 4.78 and 4.22 (an AB system, J=18 Hz, C-19H$_2$), 4.75 (d, J=10Hz, C-6H), 4.03.(m, C-3H), 3.4 (m, W=14 Hz, C-22H$_2$), 1.0 (broad singlet. C-21H$_3$), 0.88 (s, t-butyl), 0.19 (s, C-18H$_3$), 0.07 (s, Ci-CH$_3$)$_2$); IR $\nu$max 3500 (br), 2950 (s), 2900 (sh), 1640 (s), 1610 (m), 1340 (s), 1250 (s), 1090 (s), cm$^{-1}$; mass spec. molecular ion m/e=604; (analysis found: % C, 71.56; H, 8.70; N, 4.47; C$_{36}$H$_{52}$O$_4$N$_2$Si requires: % C, 71.48; H, 8.67: N>4.63).

EXAMPLE 4

6(R),19-[N,N'-phthalhydrazido]-9,10-seco-3$\beta$-acetoxy-20(S)-ethenylpregna-5(10), 7(E)-diene Methyltriphenylphosphonium bromide (60 mg, 1.2 eq) was suspended in THF (6 ml). n-Butyl lithium (1.5 M solution, 0.15 ml) was added. To the resulting orange-coloured solution, the 3$\beta$-acetoxy aldehyde from Example 2(f)(1) (100 mg) in benzene (6 ml) was added quickly. After a further 10 min, water was added and the mixture extracted with CH$_2$Cl$_2$. Acid work-up followed by purification by plc gave 75 mg (75%) of the title product. Crystalline from CH$_2$Cl$_2$/ether. m.p. 173°–175° C.; [$\alpha$]$_D$= +386° (c=0.86); $^1$Hnmr $\delta$ 8.3 (m, W=12 Hz, 2H, aryl), 7.8 (m, W=10 Hz, 2H, aryl), 5.9 (d, J=10 Hz, C-7H), 5.6–4.8 (m, C-3H, 22H, 23H.), 4.78 and 4.21 (an AB system, J=18 Hz, C-19H$_2$), 4.75 (d, J=10 Hz, C-6H), 2.03 (s, OAc), 0.95 (d, J=7 Hz, C-21H$_3$), 0.17 (s, C-18H$_3$); IR $\nu$max 2950 (m), 1740 (s), 1650 (s), 1610 (m), 1370 (s), 1350 (s), 1260 (s), 1230 (s), cm$^{-1}$; mass spec. molecular ion m/e=528; (analysis found: % C, 75.03; H, 7.72; N, 5.21; C$_{33}$H$_{40}$O$_4$N$_2$ requires % C, 74.97; H, 7.63; N, 5.30).

EXAMPLE 5

(a) Preparation of isobutylene epoxide

To methylallyl chloride (200 ml), 186 g) cooled in an ice bath was added 80% H$_2$SO$_4$ (H$_2$SO$_4$, 95%, 109 ml; H$_2$O, 40 ml, 1 eq) over a 30 min period. The temperature of the mixture was maintained between 5°–10° C. After a further 3hr the mixture was added to ice and diluted to a total volume of approx. 100 ml. The layers were separated and the organic residue distilled to remove the by-product $\beta$,$\beta$-dimethylvinyl chloride and unreacted starting material. These materials are removed below 80° C. The darkly coloured distillation residue is 1-chloro-2-methylpropan-2-ol(128a) $\delta$ 3.47 (s, 2H),2.97(s, 1H, exchanges with D$_2$O), 1.32 (s, 6H.). This material was used without further purification.

To a 500 ml round bottom flask containing KOH (200 g) in water (125 ml) at 80° C. and fitted with a mechanical stirrer and condenser, was added dropwise the crude chlorohydrin. The crude epoxide distilled directly from the reaction mixture. Redistillation gave isobutylene epoxide (48 g, 35%) b.p. 51° C. (lit. $^{128c}$52° C.); $^1$Hnmr $\delta$ 2.6 (s, 2H). 1.33 (s, 6H).

(b) 4-bromo-2-methyl-2-hydroxy-butane

To ethyl-3-bromo-propionate (21 g) in ether (150 ml) at 0° C. was added methylmagnesium bromide (3 M soln. in ether, 125 ml, excess) dropwise. After the addition was complete, the mixture was stirred for a further 2 hrs at room temperature. After cooling again to 0° C., the mixture was carefully quenched with NH$_4$Cl (30 g) in water (200 ml). The layers were separated and the ether layer washed with water until neutral, followed by brine, and dried. Evaporation gave the crude bromo-alcohol (227a) $^1$Hnmr $\delta$ 3.53 (t, J=9 Hz, 2H), 2.93 (s, 1H, exchanges with D$_2$O), 2.07 (t, J=9 Hz, 2H), 1.27 (s, 6H); [lit.$^{17}$ 3.54 (t, J=8.5 Hz, 2H), 2.65 (s, broad, 1H), 2.10 (t, J=8.5 Hz, 2H), 1.26 {s, 6H)].

(c) 4-Bromo-2-methyl-2(triethylsilyoxy)-butane

Half of the crude bromide from (b) above in ether (50 ml) containing pyridine (5 ml), imidazole (10 g) and triethylsilylchloride (10 ml) was stirred for 2 days at room temperature. Water was added. Acid work-up followed by chromatography gave 11 g (62% from the propionate) of the desired compound, homogeneous by tlc. $^1$Hnmr δ 3.52 (m, 2H), 2.03 (m, 2H), 1.25 (s, 6H), 1.2–0.2 (m, 15H); IR νmax (thin film) 3000 (s), 2950 (sh), 1460 (m), 1420 (m), 1380 (m), 1365 (m), 1230 (s), 1195 (s), 1170 (m), 1100 (s), 1040 (s), 1010 (s), 965 (m), 840 (w), 740 (s), 720 (s), cm$^{-1}$.

(d) 3-Methyl-2-buten-1-yl-triphenylphosphonium bromide

The bromide from (c) above (1 g) and triphenylphosphine (0.9 g) in benzene (4 ml) was throughly degassed, and then heated to reflux. After 3 days, the insoluble material was filtered off to give 1.2 g (85%) of phosphonium salt (228). Recrystallised from CH$_2$Cl$_2$/ETOAc. m.p. 234°–238° C. (lit.$^{119b}$ 236°–239° C.) $^1$Hnmr δ 8.17–7.67 (m, 15H, aryl), 5.18 (m, W=18 Hz), 4.73–4.2 (m, 2H), 1.67 (d, J=5 Hz, 3H), 1.31 (d, J=5 Hz, 3H); IR νmax 2900 (w), 1590 (w), 1490 (m), 1435 (s), 1110 (s), cm$^{-1}$.

(e) Methyldiphenylphosphine oxide

Methyltriphenylphosphonium bromide (6 g) was refluxed overnight with KOH (5 g) in water (70 ml). The mixture was allowed to cool to room temperature and then extracted (3x) with CH$_2$Cl$_2$. The organic layer was washed with brine, dried and the solvent removed to give the crude solid product (3.5 g) in essentially quantitative yield. Recrystallised from acetone. m.p. 113°–114° C. (lit.$^{132}$109°–111° C.); $^1$Hnmr δ 8.0–7.3 (m, 10 H, aryl), 2.03 (d, J=13 Hz, 3H); IR νmax 1440 (s), 1175 (s), cm$^{-1}$; mass spec. molecular ion m/e=216.

(f) 3-Hydroxy-3-methylbut-1-yl-diphenylphosphine oxide

Methyldiphenylphosphine oxide (1.5 g) was suspended in ether (20 ml) at 0° C. BuLi (1.2 eq) was slowly added, and an orange coloured solution formed. To this was added iso5utylene epoxide (0.8 ml, 1.3 eq). After approx. 15 min, the mixture was carefully quenched with water. This mixture was extracted with CH$_2$Cl$_2$ (2x) and the organic layer was washed with 4% aqueous HCl/brine and concentrated. The resulting yellow, oily product was dissolved in a water-ether mixture and the layers separated. The ether layer was washed once with water, and the combined aqueous fractions extracted with CH$_2$Cl$_2$ (3x). The organic layer was washed with brine and dried. The solvent was removed and the resulting colourless oil was taken up in benzene and refluxed through a soxhlet containing CaH$_2$ for 2 hr. The solvent was removed to give crude title compound (1.4 g, 70%) as an oil. $^1$Hnmr δ 8.0–7.3 (m, 10H, aryl), 2.5 (m, W=34 Hz, 2H), 1.83 (m, W=32 Hz, 3H), 1.23 (s, 6H); IR νmax (CCl$_4$) 3500 (m), 2950 (m), 1440 (s), cm$^{-1}$.

(g) 3-tetrahydropyranyloxy-3-methylbut-1-yl-diphenylphoshine oxide

The phosphine oxide from (f) abpve (1.4 g) was dissolved in dihydripyran (20 ml) and benzene (5 ml). p-Toluenesulphonic acid (10 mg) was added. After 20 hr, the mixture was concentrated, added to CH$_2$Cl$_2$ and washed with 5% aqueous NaHCO$_3$/brine and dried. Evaporation of the solvent gave the crude product (1.8 g) essentially quantitatively as a solid. Recrystallised from acetone. m.p. 146°–148° C.; $^1$Hnmr δ 8.0–7.3 (m, 10 H, aryl), 4.67 (m, W=6 Hz, THP, C-2'H), 3.67 (m, W=36 Hz, THP, C-6'H$_2$), 1.23 (s, 6H); IR νmax 2950 (m), 1440 (m), 118C (s), cm$^{-1}$; (analysis found: % C, 70.80; H, 7.73; P, 8.54; C$_{22}$H$_{29}$O$_3$P requires % C, 70.96; H, 7.85; P, 8.32.

(h) Preparation of the lithium bromide adduct of the betaine

To methyltriphenylphosphonium bromide (2.898 g) suspended in ether (50 ml) cooled to 0° C. was added butyl lithium (2.03 M soln.; 4 ml). Isobutylene epoxide (1.0 ml, 1.25 eq) was added and some insoluble material instantly formed. After stirring for 15 min, the reaction mixture was allowed to settle and the supernatant liquid was removed. The resulting solid was suspended in ether and transferred to two centrifuge tubes, and spun. The ether was removed. This process was repeated until the ether washing were colourless (usually 4x). The colourless solid material was dried to give the Li-Br adduct of the betaine(1.5 g)42%. Beilstein and lithium ion positive, flame tests. IR νmax (nujol) 3500 (br), 3000C (s), 1440 (s), cm$^{-1}$.

(i) [3-(triethylsilyloxy)-3-methylbut-1-yl]-tri-phenylphosphonium tetraphenyl borate To methyltriphenylphosphonium bromide (3 g) suspended in THF (40 ml) was added phenyl lithium (1 eq; 6 ml of a 1.5 M soln.). After 15 min isobutylene epoxide (1 ml, 1.25 eq) was added followed, after a further 5 min, by a second addition of phenyl lithium (1 eq). lo this mixture was added benzophenone (1 g; approx. 0.3 eq). After stirring for 20 min, the reaction was quenched with 48% aqueous HBr until just acidic (litmus paper). The organic solvent was removed on a rotary evaporator, water was added and the aqueous layer washed with ether, and the layers separated. The water was removed (rotary evaporator) and the resulting oil taken up in CH$_2$Cl$_2$. Aqueous work-up gave the phosphonium salt (226) (3.1 g) 58% as an oil. $^1$Hnmr δ 8.17–7.67 (m, 15H, aryl), 5.37 (broad s, —OH), 3.8 (m, W=32 Hz, C-1H$_2$), 1.8 (m, W=22 Hz, C-2H$_2$). 1.28 (s, (—CH$_3$)$_2$); IR νmax (CHCl$_3$) 3450 (s), 3000 (s), 1590 (sh), 1440 (s), cm$^{-1}$.

(j) Silylation

To the phosphonium salt from (I) above (3.7 g) in CH$_2$Cl$_2$ (70 ml) was added imidazole (3.4 g) followed by triethylsilylchloride (5 ml). After 40 hr stirring at room temperature, water was added and the mixture diluted with CH$_2$Cl$_2$. The CH$_2$Cl$_2$ solution after an acid workup was evaporated and the oily residue partitioned between water and hexane/ether. The water was evaporated and the residue taken up in CH$_2$Cl$_2$ which was washed with brine and dried to give on evaporation the salt (226b) (3.6 g, 77%) as an oil.

(k) Anion exchange

To the phosphonium salt from (j) above (3.6 g) in 95% ethanol (50 ml) was added dropwise, with stirring, a solution of sodium tetraphenyl borate (2.5 g; 1.1 eq) in water (20 ml). An oily residue is formed which solidifies on continued stirring. Filtration gives the phosphonium tetraphenyl borate salt (4.78 g, 92%) as a white, amorphous, non-hygroscopic solid which may be recrystallied from acetone/hexane/ethanol. m.p. 150°–151° C.; $^1$Hnmr δ (acetone-d$_6$) 8.2–6.8 (m, 35H, aryl), 3.53 (m, W=34 Hz, C-1H$_2$), 1.8 (m, W=24 Hz, C-2H$_2$), 1.33 (s, (—CH$_3$)$_2$), 1.25–0.5 (m, 15H, —SiEt$_3$); IR νmax 310C (s), 2950 (s), 1580 (m), 1490 (s), 1440 (s), 1110 (s), 1020 (s), cm$^{-1}$; (analysis found: % C, 81.41; H, 7.73; P, 3.93; $C_{53}H_{60}BOPSi$ requires: % C, 81.31; H, 7.73; P, 3.96.

(1)
6(R),19-[N,N'-phthalhydrazido]-9,10-seco-3β-acetoxy-25-hydroxycholesta-5(10), 7(E), 22(E)-triene Method A To methyltriphenylphosphonium bromide (2.898 g) suspended in THF (32 ml) at 0° C. was added butyl lithium (2.03 M, 4 ml). Iso-butylene epoxide (720 μl, 1 eq) was slowly added. After a further 15 min, butyl lithium (4 ml) was added. To 3 ml of this solution was added the aldehyde from Example 2(f)(1) (300 mg) in benzene (10 ml). The red colour was quickly discharged. Water was added and the mixture extracted with $CH_2Cl_2$. After acid work-up the major product was isolated by plc to give the title compound (105 mg, 31%).

Method B

The betaine from (h) above (628 mg) was suspended in ether (15 ml) and THF (10 ml). Butyl lithium was added dropwise until a stable colour was formed and then (0.75 ml, 2 eq for steroid, 1 eq for P compound) was added. To this mixture was added the aldehyde from Example 2(f)(1) (400 mg) in benzene (6 ml) (approx. min). After the addition, water was added and the mixture extracted with $CH_2Cl_2$. Work-up as above gave the title compound (155 mg, 34%).

Method C

The phosphonium salt from (h) above (280 mg, 1.5 eq) was dissolved in THF (15 ml) at 0° C. Phenyl lithium (3 eq) was added. The aldehyde (206a) (150mg, 1 eq) in benzene (6 ml) was added quickly. Tlc showed no change during 30 min and so water was added. Work-up as above, and isolation by plc gave the title product (80 mg, 47%). Crystalline from $CH_2Cl_2$/ether m.p. 175°-177° C.; $[\alpha]_D = +347°$ (c=0.83); $^1$Hnmr δ 8.3 (m, W=12 Hz, 2H, aryl), 7.8 (m, W=10 Hz, 2H, aryl), 5.9 (d, J=10 Hz, C-7H, 5.27 (m, W=10 Hz, C-3H, 22H, 23H), 4.78 and 4.21 (an AB system, J=18 Hz, C-19H$_2$), 4.75 (d, J=10 Hz, C-6H), 2.03 (s, OAc), 1.15 (s, C-26H$_3$, 27H$_3$), 0.97 (d, J=7 Hz, C-21H$_3$), 0.17 (s, C-18H$_3$); IR νmax 3800 (m), 2950 (s), 2900 (sh), 1750 (s), 1650 (s), 1610 (m), 1370 (s), 1350 (s), 1240 (s), 965 (m), cm$^{-1}$; mass spec. molecular ion m/e=600; (analysis found: % C, 73.94; H, 8.17; N, 4.59; $C_{37}H_{48}O_5N_2$ requires: % C. 73.97; H, 8 05; N, 4.66.

(m)
6(R),19-N,N'-phthalhydrazido]-9,10-seco-3β-acetoxy-25-hydroxycholesta-5(10), 7(E), 22(Z)-triene To the phosphonium salt from (i) above (1.9 g) in THF (30 ml) was added phenyl lithium (1.5 M soln., 1.7 ml, 1 eq). After a few minutes, the aldehyde (206a) (1 g) in benzene (35 ml) was added dropwise over about 1 min. After a further 3 min, water was added and the mixture diluted with $CH_2Cl_2$ and given an acid work-up. The reaction was repeated as above and the combined products chromatographed to yield 2.12 g (78%) of a crude, yellow coloured product.

The above mixture (1.4 g) was treated with AcOH:-$H_2O$:THF (8:1:1) (10 ml) for 1.5 hr. Dilution with $CH_2Cl_2$ followed by aqueous work-up, chromatography and crystallisation gave 1 g of product (85%). Further recrystallisation from $CH_2Cl_2$/ether, indicated the major component to have the following characteristics. m.p. 182°-184° C.; $[\alpha]_D = +339°$ (c=0.84); $^1$Hnmr δ 8.3 (m, W=12 Hz, 2H, aryl), 7.8 (m, W=10 Hz, 2H, aryl), 5.9 (d, J=10 Hz, C-7H), 5.27 (m, W=12 Hz, C-3H, 22H, 23H), 4.78 and 4.21 (an AB system, J=18 Hz, C-19H$_2$), 4.75 (d, J=10 Hz, C-6H), 2.03 (s, OAc), 1.17 (s, C-26H$_3$, 27H$_3$), 0.9 (d, J=7 Hz, C-21H$_3$), 0.17 (s, C-18H$_3$); IR νmax 3650 (m), 2950 (s), 2900 (sh), 1750 (s), 1650 (s), 1610 (m), 1370 (s), 1350 (s), 1240 (s), cm$^{-1}$; mass spec. molecular ion m/e=600; (analysis found: % C, 74.10; H, 8.15; N, 4.47; $C_{37}H_{48}O_5N_2$ requires: % C, 73.97; H, 8.05; N, 4.66.

(n)
6(R),19-[N,N'-phthalhydrazido]-9,10-seco-3β,25-dihydroxy-cholesta-5(10), 7(E)-diene The unsaturated side chain compound from (i) above (450 mg) in benzene (5 ml) and ethanol (5 ml) containing $NaHCO_3$ (100 mg) and 5% Pt/C (150 mg) was stirred under a hydrogen atmosphere for 24 hr. The mixture was filtered through celite and the solvent removed. To the residue, in benzene (10 ml), was added NaOH in methanol (1.25 M soln, 2 ml) and the mixture stirred for 20 min at room temperature. Acid work-up and crystalisation from $CH_2Cl_2$/ether afforded 380 mg (91%) of the title side chain saturated diol. m.p. 174°-177° C.; $[\alpha]_D = +408°$ (c=0.825); $^1$Hnmr δ 8.3 (m, W=12 Hz, 2H, aryl), 7.8 (m, W=10 Hz, 2H, aryl), 5.9 (d, J=10 Hz, C-7H), 4.78 and 4.22 (an AB system, J=18 Hz, C-19H$_2$), 4.75 (d, J=10 Hz, C-6H), 4.11 (m, C-3H), 1.22 (s, C-26H$_3$, 27H$_3$), 0.87 (broad singlet, C-21H$_3$), 0.18 (s, C-18H$_3$); IR νmax 3550 (s), 2950 (s), 2900 (sh), 1650 (s), 1610 (m), 1370 (s), 1350 (s), cm$^{-1}$; (analysis found: %C, 74.65; H, 8.66; N, 5.06; $C_{35}H_{48}O_4N_2$ requires: % C, 74.96; H, 8.63; N, 5.00.

EXAMPLE 6

General procedure for the conversion of the phthalazine-1,4-dione adduct to the corresponding 5(E), 7(E), 10(19)-triene system of the calciferol The adduct (200-600 mg) was refluxed overnight, under argon in ethanol (10 ml) and hydrazine (3 ml). After cooling to room temperature, the solvents were removed under reduced pressure and the resulting solid taken up in water (30 ml) and $CH_2Cl_2$ (30 ml). To this two-phase system under argon was added dianisyltellurium oxide (150-450 mg), $K_2CO_3$ (6 g) and 1,2-dibromotetrachloroethane (3 g), andthe mixture stirred for approx. 5 hr (tlc control). After acid work-up the mixture was chromatographed through silica gel (12 g) and the product removed from traces of tellurium oxidant by plc to give the desired vitamin D compound in 85-93% yield.

(1) 9,10-seco-3β,25-dihydroxy-cholesta-5(E), 7(E),10(19)-triene

Prepared from the adduct (240b) (200 mg) as described above, to give 131 mg (92%). Solid from ether/-hexane. m.p. 79°-81° C., $[\alpha]_D = +160°$ (c=0.735); UV λmax 273 nm (21500); $^1$Hnmr δ 6.5 and 5.83 (ABq, J=11 Hz, C-6H, 7H), 4.97 (s, C-19H), 4.67 (s, C-19H), 3.85 (m, W=14 Hz, C-3H), 1.22 (s, C-26H$_3$, 27H$_3$), 0.95 (broad singlet, C-21H$_3$), 0.55 (s, C-18H$_3$); IR νmax 3400 (m), 2950 (s), 1620 (w); mass spec. molecular ion m/e=400; (analysis found % C, 77.50; H, 10.99; $C_{27}H_{44}O_2$ requires % C, 80.94; H, 11.07: $C_{27}H_{44}O_2.H_2O$ requires. % C, 77.46: H, 11.075).

(2) 3β-(3',5'-dinitrobenzoate) ester

The above crude calciferol (1). (125 mg) in pyridine (5 ml) was treated with 3,5-dinitrobenzoyl chloride (85 mg, 1.1 eq). Water was added and the mixture diluted with ether. After acid work-up, the ester was isolated by plc (129 mg, 70%). Crystalline from ether/hexane. m.p. 105°–107° C.: $[\alpha]_D = +168°$ (c=0.97); $^1$Hnmr δ 9.13 (m, 3H, aryl), 6.62 and 5.82 (ABq, J=11 Hz, C-6H, 7H), 5.3 (m, W=14 Hz, C-3H), 5.07 (s, C-19H), 4.77 (s, C-19H), 1.23 (s, C-26H$_3$, 27H$_3$), 0.93 (broad singlet, C-21H$_3$), 0.43 (s, C-18H$_3$); IR νmax 3550 (m), 2950 (s), 2900 (sh), 1750 (s), 1640 (w), 1550 (s), 1350 (s), 1275 (s), cm$^{-1}$; (analysis found: % C, 68.62; H, 7.85; N, 4.65; C$_{34}$H$_{46}$N$_2$O$_7$ requires: % C, 68.66; H, 7.80; N, 4.71).

EXAMPLE 7

(a) 9,10-seco-3β,25-dihydroxy-cholesta-5(Z), 7(E),10(19)-triene

A solution of the 5,6-trans compound from Example 6(1) (126 mg) in benzene (30 ml) containing triethylamine (2 drops) andanthracene (25 mg) was thoroughly degassed. A hanovia lamp (number 654A36) was placed such that the outside of the water cooled jacket was 15 cm from the reaction vessel. The mixture was irradiated for 25 min and the title 5,6-cis compound isolated by plc (93 mg, 74%). Crystalline from acetone/water. m.p. 98°–100° C. (lit.$^{174}$ 95°–100° C); $[\alpha]_D = +77°$ (c=0.26); UV λmax 262 nm (19060); $^1$Hnmr δ 6.25 and 6.1 (ABq, J=11 Hz, C-6H, 7H), 5.05 (s, C-19H), 4.83 (s, C-19H), 3.9 (m, W=18 Hz, C-3H), 1.27 (s, C-26H$_3$, 27H$_3$), 0.95 (broad singlet, C-21H$_3$), 0.55 (s, C-18H$_3$); IR νmax 3500 (s), 2950 (s), 2900 (sh), 1640-]w), 1480 (m), 1380 (m), 1055 (s), cm$^{-1}$; (analysis: C$_{27}$H$_{44}$O$_2$.H$_2$O requires: %C, 77.46; H, 11.08;.found: % C, 77.29; H, 11.08. The melting point of an authentic sample supplied by Roussel Uclaf, Inc. (Romainville, France) did not depress on mixing.

(b) 3-(3',5-dinitrobenzoate) ester

Prepared as previously described in Example 6(2). Crystalline from ether/hexane. m.p. 149°–150° C. (lit.$^{172}$ 147°–148° C.); $[\alpha]_D = +90°$ (c=0.6); (analysis:C$_{34}$H$_{46}$N$_2$O$_7$ requires: % C, 68.66; H, 7.80; N, 4.71; found: % C, 68.94; H, 7.80; N, 4.52).

EXAMPLE 8

SO$_2$ adducts of 9,10-seco-3β-hydroxy-ergosta-5(Z), 7(E), 10(19), 22(E)-tetraene Sulphur dioxide was slowly plassed through a well-stirred mixture of benzene (100 ml) and water (50 ml) containing ergocalciferol (5 g), for a total of 3.5 hr. After this time, air was passed through the mixture for approx 20 min. Ether and brine were added and the layers separated. Aqueous work-up gave the known sulphur dioxide adducts (172a, 173a) which were used without further purification.

EXAMPLE 9

(a) 9,10-seco-3β-(triethylsilyloxy)-ergosta-5(E), 7(E), 10(19), 22(E)tetra-ene.

To the 3β-alcohol corresponding to the title compound (4.3 g) in CH$_2$Cl$_2$ (50 ml) was added imidazole (4 g) followed by triethylsilylchloride (3 ml). After a few minutes, water was added and the organic layer washed with water/brine and dried. Ihe required silyl ether was isolated essentially quantatively after chromatography as an oil. UV λmax 274 nm; $^1$Hnmr δ 6.45 and 5.87 (ABq, J=11 Hz, C-6H, 7H), 5.2 (m, W=9 Hz, C-22H, 23H), 4.92 (s, C-19H), 4.63 (s, C-19H), 3.82 (m, W=18 Hz, C-3H).

(b) 9,10-seco-1α-hydroxy-3β-(triethylsilyloxy)-ergosta-5(E), 7(E), 10(19), 22(E)-tetraene N-Methylmorpholine N-oxide (NMO) (6.3 g) was stirred with anhydrous MgSO$_4$ in CH$_2$Cl$_2$ (50 ml) for 30 min. Selenium dioxide (1.3 g) was stirred in methanol (50 ml) for 45 min and warmed to reflux. The above CH$_2$Cl$_2$ mixture was filtered into a solution of the 5,6-trans-ergocalciferol derivative from (a) above (5.5 g) in 1,2-dichloroethane (50 ml). This xixture was warmed to reflux and then the hot methanol mixture added, and refluxing of the whole continued for a further 35 min. The heat source was removed and the mixture diluted with CH$_2$Cl$_2$. Aqueous work-up followed by chromatography through silica gel (40 g) gave 2.66 g (47%) of the title compound as an oily product. UV λxax 274 nm; $^1$Hnmr δ 6.57 and 5.90 (ABq, J=11 Hz, C-6H, 7H), 5.25 (m, W=9 Hz, C-22, 23H), 5.08 (s, C-19H), 4.98 (s, C-19H), 4.65–3.92 (m, C-1H, 3H).

(c) 9,10-seco-1α,3β-dihydroxy-ergosta-5(E), 7(E), 10(19), 22(E)tetra-ene

The silylether from (b) above (460 mg) in THF (10 ml) was stirred for 30 min with tetrabutylammonium fluoride (460 mg). The mixture was diluted with CH$_2$Cl$_2$ and after aqueous work-up, the title diol was purified by plc to give 305 mg (84%). Crystalline from ether/hexane. m.p. 103°–105° C.; $[\alpha]_D = +172°$ (c=0.58); UV λmax 272 nm (22600); $^1$Hnmr δ 6.38 and 5.82 (ABq, J=11 Hz, C-6H, 7H), 5.18 (m, W=9 Hz, C-22H, 23H), 4.9 (m, W=9 Hz, C-19H$_2$), 4.53–3.77 (m, C-1H, 3H), 0.57 (s, C-18H$_3$); IR νmax 3500 (s), 2950 (s), 2900 (sh), 1640 (w), 1460 (m), 1375 (m), 1050 (s), 1030 (s), cm$^{-1}$; mass spec. molecular ion m/e=412; (analysis found: % C, 79.57; H, 10.71; C$_{28}$H$_{44}$O$_2$ requires: % C, 81.50; H, 10.79; C$_{28}$H$_{44}$O$_2$. ½H$_2$O requires: % C, 79.76; H, i0.76).

(d) 9,10-seco-Iu-hydroxy-3β-triethylsilyloxy-ergosta-5(Z), 7(E), 10(19), 22(E)-tetra-ene The 5,6-trans compound from (b) above (600 mg) in benzene (30 ml) containing phenazine (120 mg) and triethylamine (few drops) was photoisomerised as above for 30 min to give 400 mg (66%) of thetitle 5,6-cis vitamin. UV λmax 263nm; $^1$Hnmr δ 6.38 and 6.08 (ABq, J=11 Hz, C-6H, 7H), 5.23 (m, W=10 Hz, C-19H, 22H, 23H), 5.0 (s, C-19H), 4.6–3.92 (m, C-1H, 3H).

(e) 9,10-seco-1α,3β-dihydroxy-ergosta-5(Z), 7(E), 10(19), 22(E)-tetraene

The silyl ether derivative from (d) above (200 mg) was stirred at room temperature in THF (10 ml) with N-Bu$_4$NF (1 M soln. in THF, 2 ml) for about 30 min. Dilution with CH$_2$Cl$_2$ and aqueous work-up followed by purification by plc gave 129 mg (82%). Crystalline from ether/hexane gave the- . title compound. m.p. 141°–143° C. (lit.$^{106}$ 138°–140° C.); $[\alpha]_D = +34°$ (c=0.645); UV λmax 264nm (19100); $^1$Hnmr δ 6.35 and 6.05 (ABq, J=11 Hz, C-6H, 7H), 5.16 (m, W=14 Hz, C-19H, 22H, 23H). 4.98 (s, C-19H), 4.6–3.85 (m, C-1H, 3H), 0.55 (s, C-18H$_3$); IR νmax 3500 (s), 2950 (s), 2900

(sh), 1640 (w), 1460 (m), 1370 (m), 1060 (s), cm$^{-1}$; mass spec. molecular ion m/e=412; (analysis:$C_{28}H_{44}O_2$ requires: % C, 81.50; H, 10.75; 0, 7.76: found: % C, 81.39; H, 10.60).

EXAMPLE 10

(a) 9,10-seco-3β-acetoxy-1α-benzoyloxy-ergosta-5(E), 7(E), 10(19), 22(E)-tetra ene The 1α-hydroxy-38-triethylsilyloxy-compound from Example 9(b) (2 g) was treated with benzoyl chloride (2 ml) in pyridine (25 ml). After 30 min water was added and the mixture diluted with ether. After acid work-up, the solvent was removed and the resulting oil stirred overnight in $THF:H_2O$: AcOH; 8:1:3 (36 ml). After dilution with ether and aqueous work-up, the crude benzoate-alcohol was taken up in benzene (40 ml). Triethylamine (7 ml), acetic anhydride (3 ml) and 4-dimethylaminopyridine (15 mg) were added. After 30 min, water was added and the mixture diluted with ether. Acid work-up and chromatography through silica (10 g) gave 1.76 g 83%) of the title acetate-benzoate as an oil. $^1$Hnmr δ 8.05 (m. W=12 Hz, 2H, aryl), 7.5 (m, W=10 Hz, 3H, aryl), 6.58 (d, J=11 Hz, C-6H), 5.88 (m, W=16 Hz, C-1H, 7H), 5.15 (m, W=10 Hz, C-3H, 19H$_2$, 22H, 23H), 2.05 (s, OAc), 0.57 (s, C-18H$_3$).

(b) 6(R),19-[N,N'-phthalhydrazido]-9,10-seco-1α-benzoyloxy-3β-acetoxyergosta-5(10), 7(E), 22(E)-triene To a well-stirred suspension of phthalhydrazide (2 g) in $CH_2Cl_2$ (200 ml) at 0° C., containing the vitamin from (a) above (2 g), was added dropwise a solution of Pb(OAc)$_4$ (49) in $CH_2Cl_2$ (20 ml) and acetic acid (1 ml). After consumption of starting material (tlc control), the excess phthalhydrazide was removed by filtration. Aqueous work-up and chromatography gave 1.4 g (52% from 248b) of a 95:5 mixture of (250) and the presumed 6(S) isomer. Crystallisation from $CH_2Cl_2$/hexane gave pure title compound. m.p. 211°–213° C.; [α]$_D$= +295° (c=0.83); $^1$Hnmr δ 8.5–7.3 (m, 9H, aryl), 5.95 (m, W=14 Hz, C-1H, 7H), 5.28 (m, C-3H), 5.17 (m, W=10 Hz, C-22H, 23H), 4.92 and 4.37 (an AB system, J=18 Hz, C-19H$_2$), 4.8 (m, C-6H), 2.05 (s, OAc), 0.17 (s, C-18H$_3$): IR νmax 2950 (s), 2900 (sh), 1750 (s), 1720 (s), 1640 (s), 1610 (m), 1265 (s), 1245(s), cm$^{-1}$; mass spec. molecular ion m/e=718; (analysis found % C, 75.26; H, 7.54; N, 3.82 $C_{45}H_{54}O_6N_2$; requires: % C, 75.18; H, 7.57; N, 3.90).

EXAMPLE 11

(a) SO$_2$ adducts of 9,10-seco-3β-(t-butyldimethylsilyloxy)-ergosta5(E), 7(E), 10(19), 22(E)-tetraene The crude mixture of sulphur dioxide adducts of ergocalciferol (prepared from 5 g of ergocalciferol as described previously), in $CH_2Cl_2$ (40 ml), containing imidazole (4 g) was stirred with t-butyldimethylsilyl chloride (3.5 g). After 1.5 hr, the reaction was worked-up as described previously to give, after chromatography, 4.8 g (66%, from ergocalciferol) of the title compound as an oil epimeric at C-6. $^1$Hnmr δ 5.22 (m, W=9 Hz, C-22H, 23H), 4.64 (m, W=10 Hz, C-6H, 7H), 4.02 (m, W=16 Hz, C-3H), 3.67 (broad s, C-19H$_2$), 0.91 (s, t-Bu), 0.68+0.59 (2xs, C-18H$_3$), 0.07 s,[(Si-CH$_3$)$_2$].

(b) SO$_2$ adducts of 9,10-seco-3β-triethylsilyloxyl-ergosta-5(E),7(E), 10(19), 22(E)-tetra-ene The crude mixture of sulphur dioxide adducts of ergocalciferol (prepared from 5 g of ergociferol as described previously), in $CH_2Cl_2$ (40 ml), containing imidazole (4 g) was stirred with triethylsilylchloride (3.5 ml). After about 30 min, the reaction was worked up as described previously to give, after chromatography, 5.3 g (74% from ergocalciferol) of (210b) as an oil. $^1$Hnmr δ 5.22 (m, W=9 Hz, C-22H, 23H), 4.64 (m, W=10 Hz, C-6H, 7H), 4.02 (m, W=16 Hz, C-3H), 3.67 (broad s, C-19H$_2$).

(c) SO$_2$ adducts of 9,10-seco-3β-(t-butyldimethylsilyloxy)-20(S)-formyl-pregna-5(E), 7(E), 10(19)-triene The vitamin D$_2$ adduct from (b) above (4.7 g) was treated with ozone as described in the general procedure to give, after chromatography, 3.25 g (78%) of the aldehyde (211a). $^1$Hnmr δ 9.39 (m, C-22H), 4.66 (m, W=16 Hz, C-6H, 7H), 4.0 (m, W=16 Hz, C-3H), 3.66 (broad s, C-19H$_2$), 1.15 (d, J=6 Hz, C-21H$_3$), 0.89 (s, t-Bu), 0.71+0.62 (2xs, C-18H$_3$), 0.05 s,[(Si-CH$_3$)$_2$]; IR νmax (thin film) 2950 (s), 2900 (sh), 1720 (s), 1660 (w), 1460 (m), 1305 (s), 1250 (s), 1150 (m), cm$^{-1}$.

(d) Similarly prepared in 82% yield from (b) above was the SO$_2$ adducts of 9,10-seco-3β-(triethylsilyloxy)-20(S)-formyl-preqna-5(E), 7(E), 10(19)triene $^1$Hnmr δ 9.57 (m;C-22H), 4.67 (m, W=12 Hz, C-6H, 7H), 3.97 (m, W=16 Hz, C-3H), 3.65 (broad s, C-19H$_2$),1.15 (d, J=6 Hz, C-21H$_3$); IR νmax (thin film) 2950 (s), 2900 (sh), 1735 (s), 1660 (w), 1460 (m), 1380 (m), 1310 (s): 1150 (m), cm$^{-1}$.

EXAMPLE 12

(a) SO$_2$ adducts of 9,10-seco-3β-(t-butyldimethylsilyoxy)-20(S)-(hydroxymethyl)-pregna-5(E), 7(E), 10(19)-triene The aldehyde corresponding to the title compound (3.1 g) was reduced as described in the general procedure to the title compound in essentially quantitative yield. $^1$Hnmr δ 4.63 (m, W=12 Hz, C-6H, 7H), 4.02 (m, W=16 Hz, C-3H), 3.80–3.28 (m, C-19H$_2$, 22H$_2$), 1.05 (d, J=6 Hz, C-21H$_3$),0.87 (s, t-Bu), 0.68+0.58(2xs,C-18H$_3$), 0.05 [s,(Si-CH$_3$)$_2$];IR max (thin film) 3550(br), 2950 (s), 2900 (sh), 1660 (w), 1475 (m), 1350 (s), 1275 (s), 1155 (m), cm$^{-1}$.

(1) Similarly prepared in greater than 90% yield was the SO$_2$ adducts of 9,10-seco-3β-(triethylsilyloxy)-20(S)-(hydroxymethyl)-pregna-5(E), 7(E), 10(19)-triene $^1$Hnmr δ 4.63 (m, W=12 Hz, C-6H, 7H), 3.93 (m, W=16 Hz, C-3H), 3.77–3.17 (m, C-19H$_2$, 22H$_2$); IR νmax (thin film) 3550 (br), 2950 (s), 2900 (sh), 1660 (w), 1460(m), 1380 (m), 1305 (m), 1240 (m), 1155 (m), cm$^{-1}$.

(2) 9,10-seco-3β-(t-butyldimethylsilyloxy)-20(S)-(hydroxymethyl)pregna-5(E), 7(E), 10(19)-triene Adducts of (1) above (3 g) was stirred in refluxing methanol (50 ml) contaning NaHCO$_3$ (3 g) for 2.5 hr. Work-up as described above gave 2.36 g (90%) of the calciferol. UV λmax 274 nm; $^1$Hnmr δ 6.47 and 5.87 (ABq, J=11 Hz, C-6H, 7H), 4.92 (s, C-19H), 4.65 (s, C-19H), 4.1–3.15 (m, C-3H, 22H$_2$), 1.06 (d, J=5 Hz, C-21H$_3$), 0.9 (s, t-Bu), 0.58 (s, C-18H$_3$), 0.07 s,[(Si-CH$_3$)$_2$].

(3) Similarly prepared in 47% yield from the adducts of (1) above after chromatography was 9,10-seco-3β-(triethylsilyoxy)-20(S)-hydroxymethyl). pregna-5(E), 7(E), 10(19)-triene (267d). UV λmax 273 nm; $^1$Hnmr δ 6.43 and 5.7 (ABq, J=11 Hz, C-6H, 7H), 4.9 (s, C-19H), 4.6 (s, C-19H), 4.03-3.13 (m, C-3H, 22H$_2$)

EXAMPLE 13

9,10-seco-3β-hydroxy-20(S)-hydroxymethyl-pregna-5(E), 7(E), 10(19)triene

Method A

The phthalazine adduct from Example 3(1) (200 mg) was treated with hydrazine, followed by oxidation as described in the general procedure to give the title product (105 mg; 85%).

Method B

The phthalazine adduct from Example 3(3) (250 mg) was similarly converted to give the t-butyldimethylsilyl ether of the title product (166 mg, 90%). This material in refluxing THF (10 ml) was stirred with n-Bu$_4$NF (1 M soln in THF, 2 ml) for 1 hr. Dilution with CH$_2$Cl$_2$, followed by aqueous work-up and purification by plc gave (267c) (107 mg, 87%).

Method C

The product of Method B (160 mg) obtained via the corresponding SO$_2$ adducts was similarly converted to the title compound.

Method D

The triethylsilyl ether of the title compound (160 mg) obtained via the corresponding SO$_2$ adducts in THF (10 ml) was stirred at room temperature with n-Bu$_4$NF (1 M soln in THF, 2 ml). After about 30 min, the reaction was worked up as for (B) above, to give(267c)(101 mg, 85%).

Crystalline from CH$_2$Cl$_2$/hexane m.p. 104°-106° C.; [α]$_D$= +190° (c=0.37); UV λmax 273 nm (22640); $^1$Hnmr δ 6.5 and 5.83 (ABq, J=11 Hz, C-6H, 7H), 4.93 (s, C-19H), 4.62 (s, C-19H), 4.08-3.12 (m, C-3H, 22H$_2$), 1.05 (d, J=5 Hz, C-21H$_3$), 0.58 (s, C-IBH$_3$); IR νmax 3450 (s), 2980 (s), 2950 (sh), 1635 (w), 1450 (m), 1050 (s), 1030 (s), cm$^{-1}$; mass spec. molecular ion m/e=330; (analysis found: %C; 79.46; H, 9.94; C$_{22}$H$_{34}$O$_2$ requires % C, 79.95; H, 10.37.

EXAMPLE 14

6(R),19-[N,N'-phthalhydrazido]-9,10-seco-3β-acetoxy-20(S)-[p-toluenesulphonyloxymethyl]-pregna-5(10), 7(E)-diene The alcohol from Example 3(1)(2.275 g) in pyridine was stirred overnight with p-toluenesulphonylchloride (6.25 g) at room temperature. Water was added to the ice cooled mixture and after about 20 min, the mixture extracted with CH$_2$Cl$_2$. Acid work-up followed by crystallisation from CH$_2$Cl$_2$/ether gave 2.5 g (85%) of the required tosylate (216). m.p. 91°-92° C.; [α]$_D$= +308° (c=1.26); $^1$Hnmr δ 8.3 (m, W=12 Hz, 2H, aryl), 7.8 (m, W=10 Hz, 2H, aryl; and d, J=7 Hz, 2H, tosyl), 7.33 (d, J=7 Hz, 2H, tosyl), 5.85 (d, J=10 Hz, C-7H), 5.06 (m, C-3H). 4.78 and 4.2 (an AB system, J=18 Hz, C-19H$_2$), 4.75 (d, J=10 Hz, C-6H), 3.8 (m, W=12 Hz, C-22H$_2$), 2.43 (s, tosyl), 2.03 (s, OAc), 0.88 (d, J=5 Hz, C-21H$_3$). 0.13 (s, C-18H$_3$); IR νmax 2950 (s), 2900 (sh). 1750 (s), 1650 (s), 1610 (s), 1475 (s), 1240 (s), 1175 (s), cm$^{-1}$; mass spec. molecular ion m/e=686; (analysis found: % C, 68.09; H, 6.84; N, 4.00; S. 4.90; C$_{39}$H$_{46}$O$_7$N$_2$S requires: % C. 68.19; H, 6.75; N, 4.08; S, 4.67).

EXAMPLE 15

3-methyl-1-butyn-3-yl tetrahydropyranyl ether

3-Methyl-1-butyn-3-ol (25 ml, 21.7 g), dihydropyran (50 ml) and p-toluenesulphonic acid (5 mg) were mixed together at 0° C. for 1 hr, and then stirred at room temperature for a further 40 hr. The mixture was concentrated and the reside added to 5% aqueous NaHCO$_3$ and extracted with benzene. The organic solution was dried to give after distillation 37.3 g (86%) of the title ether. b.p. 47° C./0.8 mm Hg (lit. 30°-33° C./ 0.5 mm$^{50}$; 57° C./3.5mm$^{170}$); $^1$Hnmr δ 5.6 (m, THP C-2'H), 2.45 (s. C-1H), 1.51 (s, CH$_3$), 1.48 (s, CH$_3$); IR (thin film) 3350 s), 2950 (s), 2900 (sh), 112S (s), 1070 (s), 1030 (s), cm$^{-1}$.

EXAMPLE 16

1-mercapto-2-methyl-2-hydroxy-propane

Ethyl-2-mercapto acetate (10 ml) was added to dry ether (150 ml). The well-stirred solution was cooled to 0° C., and an ethereal solution of methyl magnesium bromide (3 M soln, 100 ml, 3.3 eq) was added dropwise over 1.5 hr. The mixture was removed from the ice bath and stirred for an additional 30 min. Ammonium chloride (18 g) in water was carefully added, and the mixture neutralised with hydrochloric acid to form 2 clear layers. The layers were separated and the ether layer washed with water/brine and dried. The solvent was removed under reduced pressure and the product distilled to give 4.4 g of the thiol. b.p. 46° C./16 mmHg (lit. 64°/26 mm$^{158a}$. 61°/22mm$^{158b}$); $^1$Hnmr δ 2.6 (d, J=9 Hz, C-1H$_2$), 2.5 (s, exchanges with D$_2$O, —OH), 1.38 (t, J=9 Hz, —SH), 1.28 (s, 6H, —(CH$_3$)$_2$); mass spec. m/e 59 (100), 73(24), 91(14).

EXAMPLE 17

6(R),19-[N,N'-phthalhydrazido]-23-thia-9,10-seco-3β-acetoxy-25-hydroxy-cholesta-5(10), 7(E)-diene To the tosylate from Example 14 (2.51 g) in THF (125 ml) and HMPTA (3 ml) was added 1-mercapto-2-methylpropan-2-ol from Example 16 (3 ml). The mixture. was degassed and NaH (50% dispersion in oil, 1.3 g) was added. After 2 hr, water was added and the mixture diluted with benzene/CH$_2$Cl$_2$. Acid work-up followed by chromatography and crystallisation from CH$_2$Cl$_2$/ether 9ave 1.71 g (77%) of the title sulphide. m.p. 187°-188° C.; [α]$_D$=348° (c=0.62); $^1$Hnmr δ 8.3 (m, W=12 Hz, 2H, aryl), 7.8 (m, W=10 Hz, 2H, aryl), 5.9 (d, J=10 Hz, C-7H), 5.07 (m, C-3H), 4.78 and 4.18 (an AB system, J=18 Hz, C-19H$_2$), 4.75 (d, J=10 Hz, C-6H), 2.58 (s, C-24H$_2$), 2.03 (s, OAc), 1.23 (s, C-26H$_3$, 27H$_3$), 0.98 (d, J=6 Hz, C-21H$_3$), 0.15 (s, C-18H$_3$); IR νmax 3600 (m), 2950 (s), 2900 (sh), 1740 (s), 1640 (s), 1610 (m), 1370 (s), 1350 (s), 1240 (s), cm$^{-1}$; mass spec. molecular ion m/e=620; (analysis found: % C, 69.47; H, 7.63; N, 4.43; S, 5.21; C$_{36}$H$_{48}$O$_5$requires: % C, 69.64; H, 7.79; N, 4.51; S, 5.17).

EXAMPLE 18

23-thia-9,10-seco-3β,25-dihydroxy-cholesta-5(E), 7(E), 10(19)-triene

Prepared from the adduct of Example 17 as described in the general procedure as an oil. UV λmax 273 nm; ¹Hnmr δ 6.52 and 5.83 (ABq, J=11 Hz, C-6H, 7H), 4.95 (s, C-19H), 4.67 (s, C-19H), 3.85 (m, W=14 Hz, C-3H), 2.63 (s, C-24H₂), 1.3 (s, C-26H₃, 27H₃), 1.1 (d, J=6 l Hz, C-21H₃), 0.58 (s, C-18H₃).

EXAMPLE 19

3-(3',5'-dinitrobenzoate)-ester

Prepared as described for the compound of Example 6(2) in 67% yield from the adduct of Example 17.

Crystalline from ether/hexane. m.p. 108°–110° C.; [α]$_D$+188° (c=0.742); UV λmax 272 nm (25,400) and 262 nm (25,400); ¹Hnmr δ 9.12 (m, 3H, aryl), 6.62 and 5.82 (ABq, J=11 Hz, C-6H, 7H), 5.33 (m, W=12 Hz, C-3H), 5.08 (s, C-19H), 4.78 (s, C-19H), 2.63 (s, C-24H₂), 1.27 (s, C-26H₃, 27H₃), 1.08 (d, J=6 Hz, C-21H₃), 0.45 (s, C-18H₃); IR νmax 3600 (m), 2950 (s), 2900 (sh), 1740 (s), 1640 (m), 1550 (s), 1350 (s), 1280 (s), 1170 (s), cm⁻¹; mass spec. molecular ion m/e=612; (analysis found: % C, 64.39; H, 7.26; N, 4.43; S, 5.11; C₃₃H₄₄O₇N₂S requires: % C, 64.68; H, 7.24; N, 4.57; S, 5.23).

EXAMPLE 20

23-thia-9,10-seco-1α-hydroxy-3β,25-bis(triethylsilyloxy)-cholesta-5(E), 7(E), 10(19)-triene To the diol of Example 18 (400 mg) in CH₂Cl (15 ml) was added imidazole followed by triethylsilylchloride (450 μl). After 7 hrs, water was added and the mixture diluted with CH₂Cl₂. Acid work-up gave the crude bis TES derivative which was used without further pruification.

Selenium dioxide (106 mg) was stirred in methanol (5 ml) for 45 min. N-methylmorpholine-N-oxide (NMO) (528 mg) was stirred in CH₂Cl₂ (5 ml) in the presence of anhydrous MgSO₄ for 30 min. The NMO solution was filtered into a solution of the crude bis TES derivative in 1,2-dichloro ethane (5 ml) and the mixture warmed to reflux. To this refluxing mixture was added the SeO₂-/methanol. After 35 min at reflux, the heating mantle was removed, the mixture diluted with CH₂Cl₂ and washed immediately with 5% aqueous NaHCO₃ and dried. Purification by plc gave 233 mg [35% from the adduct of Example 17 of the title 1α-hydroxy compound as an oil. UV λmax 274 nm; ¹Hnmr δ6.58 and 5.92 (ABq, J=12 Hz, C-6H, 7H), 5.08 (s, C-19H), 4.97 (s, C-19H), 4.67–4.03 (m, C-1H, 3H), 2.58 (s, C-24H₂), 1.32 [s, C-26H₃, 27H₃).

EXAMPLE 21

23-thia-9,10-seco-1α,3β,25-trihydroxy-cholesta-5(E), 7(E), 10(19)-triene

To the bis TES derivative from Example 20 (112 mg), in THF (5 ml), was added anhydrous tetrabutylammonium fluoride (220 mg) in benzene (3 ml). After 2.25 hr at reflux, the mixture was diluted with ethylacetate, washed with water (3x)/brine and dried. The title triol (50 mg, 68%) was isolated by plc. Crystalline from CH₂Cl₂/hexane. m.p. 129°–131° C.; [α]$_D$=+184° (c=0.2175); UV λmax 273 nm (21860); ¹Hnmr δ 6.58 ahd 5.92 (ABq, J=11 Hz, C-6H, 7H), 5.12 (s, C-19H), 5.0 (s, C-19H), 4.65–4.0 (m, C-IH, 3H), 2.67 (s, C-24H₂), 1.28 (s, C-26H₃, 27H₃), 1.12 (d, J=7 Hz, C-21H₃), 0.57 (s, C-18H₃; IR νmax 3550 (s), 2950 (s), 2900 (sh), 1640 (w), 1050 (m), 1030 (m), cm⁻¹; mass spec. molecular ion m/e=434; (analysis found: % C, 71.57; H, 9.57; S, 7.23 C₂₆H₄₂O₃S requires: % C, 71.84; H, 9.74; S, 7.38).

EXAMPLE 22

23-thia-9,10-seco-3β,25-dihydroxy-cholesta-5(Z), 7(E), 10(19)- triene

A solution of the 5,6-trans-trans vitamin from Example 20 (64 mg) in benzene (30 ml) containing triethylamine (1 drop) and antracene (15 mg) was thoroughly degassed and photoisomerised as described in Example 6(1). The mixture was irradiated for 20 min and the required title vitamin (49 mg, 77%) isolated by plc as an oil. UV λmax 262 nm; ¹Hnmr δ 6.25 and 6.0 (ABq, J=11 Hz, C-6H, 7H), 5.03 (s, C-19H), 4.82 (s, C-19H), 3.93 (m, W=18 Hz, C-3H), 2.67 (s, C-24H₂). 1.27 (s, C-26H₃), 27H₃), 1.08 (d, J=6 Hz, C-21H₃) 0.55 (s, C-18H₃).

EXAMPLE 23

The 3-(3',5'-dinitrobenzoate ester of the product of Example 22 was prepared using the method of Example 6(2). Crystalline from ether/hexane. m.p. 145°–148° C.; [α]$_D$=109° (c=0.571); UV λmax shoulders at 260 nm (24,900) and 235 nm (30,600); ¹Hnmr δ 9.08 (m, 3H, aryl), 6.33 and 6.06 (ABq, J=11 Hz, C-6H, 7H), 5.33 (m, C-3H), 5.15 (s, C-19H), 4.93 (s, C-19H), 2.65 (s, C-24H₂), 1.27 (s, C-26H₃, 27H₃), 1.08 (d, J=6 Hz, C-21H₃), 0.57 (s, C-18H₃). IR νmax 3750 (m), 2950 (s), 2900 (sh), 1750 (s), 1640 (s), 1550 (s), 1345 (s), 1280 (s), 1170 (s), cm⁻¹; mass spec. molecular ion m/e=612;(analysis found: % C, 64.7; H, 7.24; 0, 18.25; N, 4.36; S, 5.15; C₃₃H₄₄O₇N₂S requires: % C, 64.68; H, 7.24; 0, 18.28; N, 4.57; S, 5.23).

EXAMPLE 24

23-thia-9,10-seco-1α-hydroxy-3β,25-bis(triethylsilyloxy)-cholesta-5(Z), 7(E), 10(19)

The corresponding 5(E) compound of Example 20 (180 mg) in benzene (35 ml) containing phenazine (40 mg) and triethylamine (4 drops) was thoroughly degassed and irradiated as described above for 35 min. 137 mg (75%) Of the less polar 5(Z) compound was isolated as an oil by plc. UV λmax 263 nm; ¹Hnmr δ 6.35 and 6.05 (ABq, J=11 Hz, C-6H, 7H), 5.27 (s, C-19H), 4.95 (s, C-19H), 4.6–3.93 (m, C-H, 3H), 2.57 (s, C-24H₂), 1.2 (s, C-26H₃, 27H₃).

EXAMPLE 25

23-thia-9,10-seco-1α,3β,25-trihydroxy-cholesta-5(Z), 7(E), 10(19)-triene

To the corresponding bis TES derivative from Example 24 (185 mg) in THF (8 ml) was added tetrabutylammonium fluoride (1 M soln in THF, 2ml). After 1.25 hr at reflux, the mixture was diluted with CH₂Cl₂. Aqueous work-up and purification by plc gave 110 mg (90%) of the title triol. Crystalline from ether/hexane. m.p. 124°–126° C.; [α]=+54° (c=0.37); UV λmax 264 nm (17,400); ¹Hnmr δ 6.35 and 6.05 (ABq., J=11 Hz, C-6H, 7H), 5.33 (s, C-19H), 5.0 (s, C-19H). 4.65–4.0 (m, C-1H, 3H), 2.63 (s, C-24H₂), 1.27 (s, C-26H₃, 27H₃), 1.1 (d, J=6 Hz; C-21H₃), 0.55 (s, C-18H₃); IR νmax 3550 (s), 2950 (s), 2900 (sh), 1640 (w), 1050 (m), 1030 (m), cm⁻¹; mass spec. molecular ion m/e=434; (analysis found: %

C, 71.63; H, 9.61; S, 7.34 $C_{26}H_{42}O_3S$ requires: % C, 71.84; H, 9.74; S, 7.38).

EXAMPLE 26

23-thia-9,10-seco-1α,3β-bis(3′,5′-dinitrobenzoyloxy)-25-hydroxycholesta-5(Z), 7(E),10(19)-triene To the triol from Example 25 (75 mg) in pyridine (3 ml) and benzene (5 ml) was added 3,5-dinitrobenzoylchloride (85 mg). Water was added and the mixture diluted with ether. Work-up as in Example6(2)and purification by plc gave 97 mg (68%) of the unstable bis (dinitrobenzoate). $^1$Hnmr δ 9.8 (m, 6H, aryl), 6.62 (d, J=11 Hz, C-6H), 6.12–5.42 (m, C-1H, 3H, 7H: (s, C-26H$_3$, 27H$_3$), 1.08 (broad singlet. C-21H$_3$), 0.22 (s, C-18H$_3$).

EXAMPLE 27

23-thia-9,10-seco-1α,3β-25-trihydroxy-cholesta-5(Z), 7(E), 10(19)-triene-23,S-oxides The sulphide from Example 25 (100 mg) in methanol (10 ml), ether and water (2 ml) was stirred at room temperature with sodium metaperiodate (50 mg). After hr, a further addition of oxidant (20 mg) was made. After a total of 5 hr, the mixture was diluted with $CH_2Cl_2$. Aqueous work-up followed by plc gave 92 mg (89%) of the title sulphoxide mixture. Solid from acetone, methanol/hexane, ether. m.p. 148°–155° C.; $[α]_D=77°$ (c=0.691); UV λmax 263 nm (18150); $^1$nmr δ 6.35 and 6.05 (ABq, J=11 Hz, C-6H, 7H), 5.33 (s, C-19H), 5.0 (s, C-19H), 4.62–3.72 (m, C-1H, 3H, —OH, exchanges with $D_2O$), 2.83 and 2.75 (broad singlets, C-24H$_2$), 1.52 and 1.38 (C-26H$_3$, 27H$_3$), 1.23 (broad singlet, C-21H$_3$), 0.6 (s, C-18H$_3$); IR νmax 3500 (s), 3300 (s), 2950 (s), 2900 (sh), 1620 (w), 1380 (s), 1220 (s), 1070 (s), 1050 (s), 1030 (s), 1000 (s), cm$^{-1}$; mass spec. molecular ion m/e=450; (analysis found: % C, 69.05; H, 9.44; S, 7.13 $C_{26}H_{42}O_4S$ requires: % C, 69.29; H, 9.39; S, 7.12).

EXAMPLE 28

23-oxa-9,10-seco-3β,25-dihydroxy-cholesta-5(E), 7(E), 10(19)-triene

The silyl ether from Example 52 (160 mg) was stirred with n-Bu$_4$NF (1 M soln in THF, 1 ml) in refluxing THF (5 ml) for 40 min. Dilution with $CH_2Cl_2$, followed by aqueous work-up and purification by plc gave the title compound (102mg, 82%). UV λmax 274nm; $^1$Hnmr δ 6.47 and 5.85 (ABq, J=11 Hz, C-6H, 7H), 4.9 (s, C-19H), 4.63 (s, C-19H), 3.83 (m, W=18 Hz, C-3H), 3.58–3.07 (m, C-22H$_2$), 3.18 (s, C-24H$_2$). 1.2 (s, C-26H$_3$, 27H$_3$), 1.03 (d, J=6 Hz, C-21H$_3$), 0.58 (s, C-18H$_3$).

EXAMPLE 29

The 3-(3′-5′-dinitrobenzoate) ester of the product of Example 28 was prepared as described previously for Ex. 6(2). Crystalline from ether/hexane. m.p. 75°–77° C.; $[α]_D=+176°$ (c=0.58); $^1$Hnmr δ 9.15 (m, 3H, aryl), 6.58 and 5.78 (ABq, J=11 Hz, C-6H, 7H), 5.3 (m, W=12 Hz, C-3H), 5.03 (s, C-19H), 4.73 (s, C-19H), 3.57–3.07 (m, C-22H$_2$), 3.2 (s, C-24H$_2$), 1.22 (s, C-26H$_3$, 27H$_3$), 1.02 (d, J=6 Hz, C-21H$_3$), 0.47 (s, C-18H$_3$); IR νmax 3500 (m), 2950 (s), 2900 (sh), 1730 (s), 1640 (m), 1550 (s), 1460 (m), 1340 (s), 1270 (s), 1165 (m), cm$^{-1}$; mass spec. molecular ion m/e=596; (analysis found: % C, 66.31; H, 7.55; N, 4.56; $C_{33}H_{44}O_8N_2$ requires: % C, 66.42; H, 7.43; N, 4.70).

EXAMPLE 30

23-oxa-9,10-seco-3β-(t-butyldimethylsilyloxy)-25-hydroxy-cholesta-5(Z), 7(E), 10(19)-triene The corresponding 5(E) compound from Example 52 (160 mg) in benzene (30 ml) and triethylamine (3 drops) containing phenazine (35 mg) was thoroughly degassed and irradiated as described above for 30 min. Purification by plc gave (273a) (138 mg, 86%). UV max=263 nm; $^1$Hnmr δ 6.25 and 6.0 (ABq, J=11 Hz, C-6H, 7H), 5.05 (s, C-19H), 4.82 (s, C-19H), 3.92 (m, W=18 Hz, C-3H), 3.62–3.10 (m,C-22H$_2$), 3.20 (s, C-24H$_2$), 1.23 (s, C-26H$_3$, 27H$_3$), 1.03 (d, J=6 Hz, C-21H$_3$), 0.91 (s, t-Bu), 0.58 (s, C-18H$_3$), 0.05 [s,(Si-CH$_3$)$_2$].

EXAMPLE 31

23-oxa-9,10-seco-3β,25-dihydroxy-cholesta-5(Z), 7(E), 10(19)-triene

The corresponding 3-t-butyldimethylsilyl ether from Example 30 (138 mg) was stirred with n-Bu$_4$NF (1 M soln in THF, 2 ml) in refluxing THF (5 ml). After 45 min, the mixture was diluted with $CH_2Cl_2$. Aqueous work-up followed by purification by plc gave the diol (273b) (91 mg, 85%) as an oil. UV λmax 263 nm; $^1$Hnmr δ 6.24 and 6.04 (ABq, J=11 Hz, C-6H, 7H), 5.03 (s, C-19H), 4.83 (s, C-19H), 3.92 (m, W=18 Hz, C-3H), 3.57–3.12 (m, C-22H$_2$), 3.25 (s, C-24H$_2$), 1.22 (s, C-26H$_3$, 27H$_3$), 1.03 (d, J=6 Hz, C-21H$_3$), 0.57 (s, C-18H$_3$).

EXAMPLE 32

The 3-(3′,5′-dinitrobenzoate) ester of the product of Example 31 was prepared as in Example 6(2). Crystalline from ether/hexane m.p. 136°–138° C.; $[α]_D=+101°$ (c=0.615); $^1$Hnmr δ 9.12 (m, 3H, aryl), 6.22 and 6.01 (ABq, J=11 Hz, C-6H, 7H), 5.23 (m, W=18 Hz, C-3H), 5.1 (s, C-19H), 4.92 (s, C-19H), 3.57–3.1 (m, C-22H$_2$), 3.2 (s, C-24H$_2$), 1.22 (s, C-26H$_3$, 27H$_3$), 1.05 (d, J=6 Hz, C-21H$_3$), 0.53 (s, C-18H$_3$); IR νmax 3550 (m), 2950 (s), 2900 (sh), 1750 (s), 1650 (m), 1555 (s), 1470 (m), 1350 (s), 1280 (s), cm$^{-1}$; mass spec. molecular ion m/e=596; (analysis found: % C, 66.34; H, 7.37; N, 4.61; $C_{33}H_{44}O_8N_2$ requires: % C, 66.42; H, 7.43., N, 4.70).

EXAMPLE 33

23-oxa-9,10-seco-3β-(t-butyldimethylsilyloxy)=25-(triethylsilyloxy)-cholesta-5(E),7(E),10(19)-triene The 25-hydroxy compound from Example 52 (300 mg) in $CH_2Cl_2$ (10 ml) was treated with triethylsilylchloride (130 μl) in the presence of imidazole (200 mg) for 16 hrs. Acid work-up gave the title bis silylated calciferol (274) which was used in the next step without further purification.

EXAMPLE 34

23-oxa-9,10-seco-1α-hydroxy-3β-(t-butyldimethylsilyloxy}-25-(triethylsilyloxy)-cholesta-5(E), 7(E), 10(19)-triene Selenium dioxide (60 mg) was stirred in methanol (4 ml) for 45 mins. NMO (300 mg) was stirred in $CH_2Cl_2$ (4 ml) in the presence of anhydrous $MgSO_4$ for 30 min. The NMO solution was filtered into a solution of the bis silyl ether from Example 33 in 1,2-dichloroethane (4 ml) and the mixture warmed to reflux. To this refluxing mixture was added the $SeO_2$/methanol mixture. After 23 min, the heating mantle was removed and the product worked up and isolated as described previously to give 190 mg [51% based on Example 52] of the title 1α-hydroxylated product. UV λ max 274 nm; ¹Hnmr δ 6.55 and 5.88 (ABq, J=12 Hz, C-6H, 7H), 5.1 (s, C-19H), 5.0 (s, C-19H), 4.75–4.02 (m, C-1H, 3H), 3.65–3.12 (m, C-22H₂), 3.25 (s, C-24H₂).

EXAMPLE 35

23-oxa-9,10-seco-1α,3β,25-trihydroxy-cholesta-5(E),-7(E),10(19)-triene

The bis silyl ether from Example 34 (190 mg) in THF (6 ml) was refluxed with nBu₄NF (1 M solution in THF, 2 ml) for 1 hr. The mixture was diluted with CH₂Cl₂. Aqueous work-up gave the title triol (103 mg; 84%) after purification by plc. Crystalline from chloroform/hexane. mp 141°–144° C., [α]$_D$32 +144° (c=0.355); UVλ max 272 nm (20554); ¹Hnmr (400MHz) δ 6.58 (d, J=12 Hz), 5.89 (d, J=12 Hz), 5.13 (s, C-19H), 4.98 (s, C-19H), 4.50 (m, W=12 Hz, C-1H), 4.26 (m, W=20 Hz, C-3H), 3.43 (m, 1H), 3.30–3.15 (m, C-22H₂, 24H₂), 1.20 (s, C-26H₃, 27H₃). 1.02 (d, J=6 Hz, C-21H₃), 0.58 (s, C-18H₃); IR νmax 3500 (s), 2950 (s), 2900 (sh), 1640 (w), 1450 (m), 1380 (m), 1360 (m), 1045 (s), cm⁻¹; mass spec. molecular ion m/e =418; (analysis found: % C, 74.76; H, 10,33: C₂₆H₄₂O₄ requires % C, 74.60; H, 10.11).

EXAMPLE 36

23-oxa-9,10-seco-1α-hydroxy-3β-(t-butyldimethylsilyloxy)-25-(triethylsilyloxy)-cholesta-5(Z), 7(E), 10(19)-triene The corresponding 5(E) compound from Example 35 (200 mg) in benzene (35 ml) containing phenazine (40 mg) and triethylamine (4 drops) was irradiated with the hanovia lamp as described previously for 35 min to give, after purification by plc, 155 mg (78%) of the title compound as a less polar, oily product. UV λmax 263 nm; ¹Hnmr δ 6.30 and 6.01 (ABq, J=12 Hz, C-6H, 7H), 5–23 (s, C-19H), 4.97 (s, C-19H), 4.67–3.9 (m, C-1H, 3H), 3.53–3.07 (m, C-22H₂), 3.17 (s, C-24H₂).

EXAMPLE 37

23-oxa-9,10-seco-1α,3β,25-trihvdroxy-cholesta-5(Z), 7(E), 10(19)-triene

The bis silyl ether from Example 36 (155 mg) and n-Bu₄NF (1 M soln in THF, 2 ml) were stirred together in refluxing THF (5 ml) for 1 hr. Dilution with CH₂Cl₂ followed by aqueous work-up and purification by plc gave the title triol (252a) (77 mg, 77%). Crystalline from ether/hexane. m.p. 121°–123° C.: [α]$_D$ = +47° (c=0.6); ¹Hnmr δ UV λmax 264 nm (17200); ¹Hnmr δ 6.37 and 6.05 (ABq, J=11 Hz, C-6H, 7H), 5.33 (s, C-19H), 5.0 (s, C-19H), 4.57–3.87 (m, C-1H, 3H), 3.6–3.1 (m, C-22H₂), 3.23 (s, C-24H₂), 1.23 (s, C-26H₃, 27H₃), 1.05 (d, J=6 Hz, C-21H₃), 0.58 (s, C-18H₃); IR νmax 3500 (s). 2950 (s), 2900 (sh), 1640 (w), 1450 (m), 1380 (m), 1360 (m), 1045 (s), cm⁻¹; mass spec. molecular ion m/e=418; (analysis found: % C, 74.47; H, 9.97; C₂₆H₄₂O₄ requires: % C, 74.60; H, 10.11).

EXAMPLE 38

9,10-seco-3β-(triethylsilyloxy)-20(S)-(p-toluenesulphonyloxymethyl}pregna-5(E), 7(E), 10(19)-triene.

Method A

To the hydroxy compound from Example 13(D)(400 mg) in pyridine (5 ml) was added tosylchloride (350 mg) and the mixture stirred overnight at room temperature. Water was added and the mixture diluted with ether. Acid work-up gave, after purification by plc, 310 mg (58%) of the title tosylate ¹Hnmr δ 7.73 (d, J=8 Hz, 2H, aryl), 7.28 (d, J=8 Hz, 2H, aryl), 6.43 and 5.81 (ABq, J=11 Hz, C-6H, 7H), 4.92 (s, C-19H), 4.63 (s, C-19H), 4.2–3.57 (m, C-3H, 22H₂), 2.48 (s, aryl-CH₃); IR νmax (thin film) 2960 (s), 2900 (sh), 1600 (w), 1460 (m), 1360 (s), 1190 (s), 1175 (s), 1090 (s), cm⁻¹.

Method B

The crude SO₂ adducts of 9,10-seco-3β-triethylsilyloxy-20(S)-(hydroxymethyl)-pregna-5(E), 7(E), 10(19)-triene from Example 12(1)(3.2 g) was stirred overnight in pyridine (40 ml) at 5° C. with p-toluenesulphonyl chloride (4 g). The reaction was cooled to 0° C., water added and, after a few minutes, the mixture was diluted with Et₂O. After an acid work-up, the crude oily product (281) was taken up in ethanol (100 ml) and refluxed in the presence of NaHCO₃ (49) for 1 hr. The mixture was concentrated and partioned between CH₂Cl₂/water/brine. The organic solution was dried and chromatographed to give 2.64 g (70%) of the required vitamin (278c) nmr and IR identical to the product obtained by Method A.

EXAMPLE 39

9,10-seco-3β-hydroxy-20(S)-[fluoromethyl]-preqna-5(E), 7(E), 10,(19)-triene

The tosylate from Example 38 (200 mg) in THF (5 ml) was refluxed for 45 min in the presence of n-Bu₄NF (1 M soln in THF, 1 ml). The mixture was diluted with CH₂Cl₂. Aqueous work-up followed by purification by plc gave 70 mg (63%) of the title fluoride (279). ¹Hnmr δ 6.5 and 5.83 (ABq, J=11 Hz, C-6H, 7H), 4.97 (s, C-19H), 4.7 (br, s, C-19H, 22H), 4.2–3.6 (m, C-3H, 22H), 1.1 (d,J=6 Hz, C 21H₃), 0.6 (s, C-18H₃)

EXAMPLE 40

9,10-seco-1α-hydroxy-3β-(triethylsilyloxy)-20(S)-(p-toluenesulphonyloxymethyl)-pregna-5(E), 7(E), 10(19)-triene Selenium dioxide (56 mg) was stirred in acetonitrile (3.5 ml) for 45 min. NMO (280 mg) was stirred in CH₂Cl₂ (3.5 ml) in the presence of anhydrous MgSO₄ for 30 min. The NMO solution was filtered into a solution of the 1-desoxy compound from Example 38 (308 mg) in 1,2-dichloroethane (3.5 ml) and the mixture warmed to reflux. To this was added the SeO₂/CH₃CN mixture, and refluxing continued for a further 5.5 min. The reaction mixture was cooled in an ice bath, diluted with CH₂Cl₂ and worked up as described previously to give 180 mg (57%) of thc title 1-hydroxy compound. ¹Hnmr δ 7.73 (d, J=8 Hz, 2H, aryl), 7.28 (d, J=8 Hz, 2H, 6.43 and 5.81 (ABq, J=11 Hz, C-6H, 7H), 5.03 (s, C-19H), 4.93 (s, C-19H), 4.63–3.6 (m, C-1H, 3H, 22H₂), 2.48 (s, aryl-CH₃).

EXAMPLE 41

9,10-seco-1α,3β-dihydroxy-20(S)-(p-toluenesulphonyloxymethyl)-pregna-5(E), 7(E), 10(19

The 3-triethylsilylether derivative from Example 40 (180 mg) in THF (5 ml) containing n-Bu₄NF (1 M soln in THF, 0.4 ml) was stirred for 15 min. The mixture was diluted with $CH_2Cl_2$. An aqueous work-up and purification by plc gave 118 mg (81%) of the title diol. Solid from $CH_2Cl_2$hexane m.p. 97°–99° C.; $[\alpha]D = +132°$ (c=0.57); UV $\lambda$max 272 nm (23360) and 218 nm (15920); $^1$Hnmr $\delta$ 7.73 (d, J=8 Hz, 2H, aryl), 7.28 (d, J=8 Hz, 2H, aryl), 6.43 and 5.81 (ABq, J=11 Hz, C-6H, 7H), 5.03 (s, C-19H), 4.93 (s, C-19H), 4.63–3.53 (m, C-1H, 3H, 22H$_2$), 2.5 (s, aryl-CH$_3$). 1.02 (d, J=6 Hz, C-21H$_3$), 0.57 (s, C-18H$_3$); IR $\nu$max 3500 (s), 2950 (s), 2900 (sh), 1600 (w), 1450 (m), 1355 (s), 1190 (s), 1175 (s), cm$^{-1}$.

EXAMPLE 42

9,10-seco-1$\alpha$-hydroxy-3$\beta$-(triethylsilyoxy)-20(S)-(p-toluenesulphonyloxymethyl)-preqna-5(Z), 7(E), The corresponding 5(E) compound from Example 40 (225 mg) in benzene (35 ml) containing triethylamine (3 drops) was irradiated as described above with anthracene (45 mg) as triplet sensitiser for 30 min to give, after plc, 185 mg (82%) of the title compound. UV $\lambda$max 263 nm and 216 nm; $^1$Hnmr $\delta$ 7.73 (d, J=8 Hz, 2H, aryl), 7.3 (d, J=8 Hz, 2H, aryl), 6.28 and 5.98 (ABq, J=11 Hz, C-6H, 7H), 5.28 (s, C-19H), 4.92 (s, C-19H), 4.55–3.58 (m, C-1H, 3H, 22H$_2$), 2.45 (s, aryl-CH$_3$).

EXAMPLE 43

9,10-seco-1$\alpha$,3$\beta$dihydroxy-20(S)-(p-toluenesulphonyloxymethyl)pregna-5(Z), 7(E), 10(19)

The silyl ether from Example 43 (135mg) in THF (5 ml) containing n-Bu$_4$NF (1 M soln in THF, 0.32 ml) was stirred for 15 min at room temperature. Dilution with $CH_2Cl_2$ aqueous work-up and purfication by plc gave the title diol (110 mg, 73%). UV max 263 nm (7427) and 216 nm (18672); $^1$Hnmr $\delta$ 7.68 (d, J=8 Hz, 2H, aryl), 7.23 (d, J=8 Hz, 2H, aryl), 6.28 and 5.97 (ABq, J=11 Hz, C-6H, 7H), 5.27 (s, C-19H), 4.93 (s, C-19H), 4.57–3.6 (m, C-1H, 3H, 22H$_2$), 2.45 (s, aryl-CH$_3$), 1.05 (d, J=6 Hz, C-21H$_3$), 0.52 (s, C-18H$_3$)

EXAMPLE 44

1-amino-2-methyl-2-hydroxy-propane

To a well-stirred mixture of lithium aluminium hydride (12 g) in ether (200 ml) at 0° C. was added dropwise over 1 hr a solution of acetone cyanohydrin (11.2 g, 12 ml) in ether (50 ml) The mixture was stirred at room temperature overnight. After cooling to 0° C., water (24 ml) was cautiously added dropwise. After the quenching was complete, anhydrous Na$_2$SO$_4$ (65 g) was added and stirring at room temperature was continued for a further 2.5 hr. The solid was filtered off and the ether evaporated to give, after distillation, 4.8 g (41%) of the title compound as a viscous, colourless liquid. b.p. 74°–76° C./14mm Hq (lit.$^{169}$ 62°–64° C./13mm Hg) $n_D^{20}$=1.4463 (lit.$^{169}$ $n_D^{20}$=1.4467); $^1$Hnmr $\delta$ 2.6 (s, 2H), 1.87 (s, 3H, exchanges with D$_2$O), 1.2 (s, 6H); IR $\nu$max (thin film) 3400 (s). 3000 (m), 1600 (m), 1475 (m), 1380 (m), 1360 (m), 1220 (m), 1170 (m), 1110 (m), 960 (m), cm$^{-1}$.

EXAMPLE 45

23-aza-9,10-seco-1$\alpha$,3$\beta$,25-[rihydroxy-cholesta-5(Z), 7(E), 10(19)-triene A solution of the tosylate from Example 44 (100 mg) in 1-amino-2-methyl-2-hydroxy-propane (0.5 ml) was degassed and then stirred under argon at 50°–55° C. for 6 hr amd then at room temperature for a further 12 hr. The solution was diluted with $CH_2Cl_2$ and washed with water/brine and dried to give, after purification by plc, 44 mg (53%) of the title triol. $[\alpha]_D = +24°$; UV $\lambda$max 264 nm (15400); $^1$Hnmr $\delta$ 6.38 and 6.07 (ABq, J=11 Hz, C-6H, 7H), 5.35 (s, C-19H), 5.02 (s, C-19H), 4.67–3.93 (m, C-1H, 3H). 2.5 (s, C-24H$_2$), 1.2 (s, C-26H$_3$, 27H$_3$), 1.02 (d, J=6 Hz, C-21H$_3$), 0.57 (s, C-18H$_3$); IR $\nu$max 3500 (s), 2950 (s), 2900 (sh), 1640 (w), 1460 (m), 1380 (m), 1055 (m), cm$^{-1}$; mass measurement found: 417.3242; C$_{26}$H$_{43}$O$_3$N requires: 417.3243.

EXAMPLE 46

23-aza-9,10-seco-1$\alpha$,3$\beta$,25-trihydroxy-cholesta-5(Z), 7(E), 10(19)-triene-23-N-acetyl The crude amine from Example 45 derived from the tosylate (100 mg) as described above, in methanol (5 ml) containing K$_2$CO$_3$ (500 mg) was treated with acetic anhydride (0.2 ml). The mixture was diluted with $CH_2Cl_2$ washed with brine and dried to give, after plc, 50 mg [55% from tosylate] of the title amide. Solid from $CH_2Cl_2$hexane. m.p. 107°–109° C.; $[\alpha]D = -14°$ (c=0.49); UV $\lambda$max 263 nm (16275); $^1$Hnmr $\delta$ 6.37 and 6.05 (ABq, J=11 Hz, C-6H, 7H), 5.33 (s, C-19H), 5.0 (s, C-19H), 4.65–4.02 (m, C-1H, 3H), 3.4 (s, C-24H$_2$), 2.17 (s, acetyl), 1.22 (s, C-26H$_3$, 27H$_3$), 0.95 (d, J=7 Hz, C-21H$_3$), 0.6 (s, C-18H$_3$); IR $\nu$max 3550 (s), 2950 (s), 2900 (sh), 1640 (s), 1460 (m), 1380 (m), 1055 (m), cm$^{-1}$; (analysis found: % C, 70.80; H, 10.12; N, 2.77; C$_{28}$H$_{45}$O$_N$ requires: C, 73.16; H, 9.87; N, 3.05; C$_{28}$H$_{45}$O$_4$N.H$_2$O requires: % C, 70.40; H, 9.92; N, 2.93).

EXAMPLE 47

9,10-seco-3$\beta$,25-dihydroxy-cholesta-5(E), 7(E), 10(19)-triene

Magnesium turning were washed with diluted HCl/water/acetone/ether and dried in vacuo for 24 hr. The 1-bromo-4-methyl-4-triethylsilylbutane (1 g) in freshly distilled (from LiAlH$_4$) THF (10 ml) containing magnesium metal (82 mg) was refluxed for 2 hr.

Cuprous iodide (100 mg) was placed in a flask and purged with argon, whilst cooling to 0° C. To this was added the above Grignard solution (5 ml), and the purple coloured mixture stirred for an additional 30 min at 0° C. A solution of the tosylate (278c) (200 mg) in ether (2 ml) was added and the mixture stirred for 40 min at room temperature. Water was added and the reaction mixture extracted with ether. After an acid work-up, the non-polar product was isolated by plc contaminated with large quantities of low molecular weight alkyl residues. This mixture was stirred with n-Bu$_4$NF (1 M soln in THF, 2 ml) in refluxing THF (5 ml) for 2 hr. Dilution with $CH_2Cl_2$ followed by aqueous work-up and purification by plc gave IIOmg [82% from tosylate (278c)] of this previously described title diol. The physical and spectral properties of this material were identical in all respects totheproduct obtained from the phthalazine adduct.

EXAMPLE 48

9,10-seco-3$\beta$,25-dihyroxy-cholest-5(Z), 7(E), 10(19)-triene

The product from Example 47 (100 mg) in benzene (30 ml) and triethylamine (3 drops) containing anthracene (25 mg) was thoroughly degassed and irradiated for 1 hr as described above to give, after purification by plc, the title 5(Z) compound (90 mg, 82%). The physical and spectral properties of this material were iden-

EXAMPLE 49

9,10-seco-1α,3β-bis(triethylsilyloxyy)-20(S)-(p-toluenesulphonyloxymethyl)-pregna-5 (Z), 7(E), 10(19)-triene The tosylate (276b) (105 mg) in $CH_2Cl_2$ (5 ml) containing imidazole (75 mg) and triethylsilychloride (45 µl) was stirred at room temperature for about 15 min. Water was added and the mixture diluted with $CH_2Cl_2$ Acid work-up gave the non-polar title bis silyl ether which was used without further purification.

EXAMPLE 50

9,10-seco-1α,3β,25-trihydroxy-cholesta-5(Z), 7(E), 10(19)-triene

To the alkyl copper reagent at 0° C. prepared exactly as described above, was added a solution of the above tosylate (276c) in THF (3 ml) and the mixture stirred at room temperature for 25 min. Work-up and purification as in Example 6(1) gave the tris triethylsilyl derivative contaminated with large quantities of low molecular weight alkyl residues. This mixture was treated with n-Bu₄NF (1 M soln in THF, 4 ml) in THF (5 ml) for 20 min at room temperature followed by 1.5 hr at reflux to give, after the usual work-up and purification by plc, a mixture of the title steroidal triol [(38 mg. 63% from (276b)] contaminated with the iso-pentane diol (10 mg). Dissolution of this mixture in $CHCl_3$ gave the required product as its crystalline $CHCl_3$ solvate (25 mg). m.p. 99°-105° C. (lit. 106°-112° C$^{142}$, 103°-106° C.$^{138}$); [α]$^D$ (Et₂O) = +35° (c=0.86); UV λmax 264 nm (16820); ¹Hnmr δ (acetone-d6) 8.07 (s, CHCl₃), 6.35 and 6.18 (ABq, J=12 Hz, C-6H, 7H), 5.38 (s, C-19H), 4.93 (s, C-19H), 4.7-4.07 (m, C-1H, 3H), 1.2 is, C-26H₃, 27H₃), 1.0 (broad singlet, C-21H₃). 0.6 (s, C-18H₃); IR νmax 3500 (s), 2950 (s), 2900 (sh), 1640 (w), 1480 (m), 1440 (m), 1380 (m), 1360 (m), 1140 (m), 1050 (s).

EXAMPLE 51

23-oxa-9,10-seco-3β-(t-butyldimethylsilyloxy)-25-hydroxy-5(E), 7(E), 10(19)-triene The 22-hydroxy compound (167b) (425 mg) in benzene (5 ml) was refluxed with isobutylene epoxide (1 ml) in the presence of dibenzo-18-crown-6 (100 mg) and potassium t-butoxide (500 mg) for 55 min. Water was added and the mixture diluted with $CH_2Cl_2$. The organic layer was washed with aqueous $K_3PO_4$/water/5% aqueous $NaHCO_3$/brine and dried. Purification by plc gave 330 mg (67%) of the slightly less polar oily product. ¹Hnmr δ 6.45 and 5.85 (ABq, J=12 Hz, C-6H, 7H), 4.9 (s, C-19H), 4.63 (s, C-19H), 3.92 (m, W=18 Hz, C-3H), 3.63-3.12 (m, C-22H₂), 3.22 (s, C-24H₂), 1.23 (s, C-26H₃, 27H₃), 1.05 (d, J=6 Hz, C-21H₃), 0.92 (s, t-Bu), 0.6 (s, C-18H₃), 0.05 s,[(Si-CH₃)₂].

I claim:

1. Compounds of the general formula:

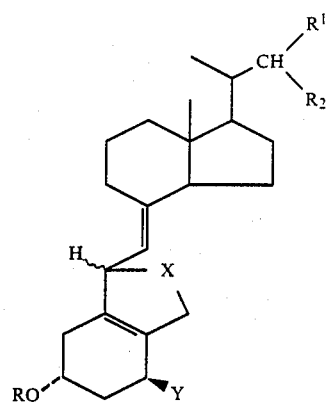

wherein R represents a hydrogen atom or a hydroxyl protecting group, Y represents a hydrogen atom, a hydroxyl group or a protected hydroxyl group, X represents the residue of a dienophile and R¹ represents a halogen atom, hydroxyl or tosyloxy group or a group of formula: Z—R³ where Z represents —O—, —S—, —NR⁴ or —SO—, where R³ represents a straight or branched aliphatic group having 1-12 carbon atoms which may carry one or more substituents selected from halogen atoms, hydroxyl groups and protected hydroxy groups and R⁴ represents hydrogen or a straight or branched aliphatic group having 1-12 carbon atoms which may carry one or more substituents selected from halogen atoms, hydroxyl groups and protected hydroxy groups and R² represents a hydrogen atom or R¹ and R² together represent an oxo group.

2. Compounds as claimed in claim 1 in which the dienophile is $SO_2$ or a diacylazo compound.

3. Compounds of general formula IV or IVa:

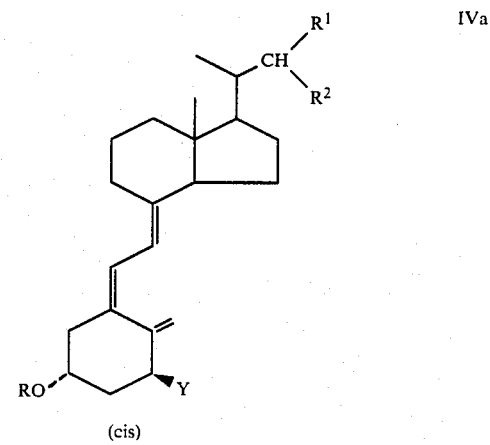

(cis)

-continued

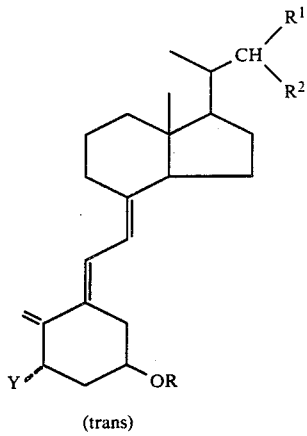

(trans)

wherein R represents a hydrogen atom or a hydroxyl protecting group, Y represents a hydrogen atom, a hydroxyl group or a protected hydroxyl group, $R^1$ represents a halogen atom, hydroxyl or tosyloxy group or a group of formula: $Z\text{-}R^3$ where Z represents —O—, —S—, —NR$^4$, or —SO—, where $R^3$ represents a straight or branched aliphatic group having 1–12 carbon atoms which may carry one or more substituents selected from halogen atoms, hydroxyl groups and protected hydroxy groups and $R^4$ represents hydrogen or a straight or branched aliphatic group having 1–12 carbon atoms which may carry one or more substituents selected from halogen atoms, hydroxyl groups and protected hydroxy groups and $R^2$ represents a hydrogen atom or $R^1$ and $R^2$ together represent an oxo group.

4. Compounds of general formulae IV or IVa as claimed in claim 3 wherein $R^1$ represents a halogen atom, a hydroxyl or tosyloxy group or a group of formula:

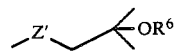

in which Z' represents —O—, —S—, —NH— or —SO— and $R^6$ represents a hydrogen atom or a hydroxyl protecting group and $R^2$ represents a hydrogen atom.

5. Compounds of general formula I as claimed in claim 1 wherein $R^1$ represents a halogen atom, a hydroxyl or tosyloxy group or a group formula:

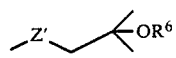

in which Z' represents —O—, —S—, —NH— or —SO— and $R^6$ represents a hydrogen atom or a hydroxyl protecting group and $R^2$ represents a hydrogen atom.

* * * * *